(12) United States Patent
Rudi et al.

(10) Patent No.: US 8,889,358 B2
(45) Date of Patent: Nov. 18, 2014

(54) METHODS OF AMPLIFYING A TARGET SEQUENCE OF A 16S RRNA OR 16S RDNA IN A PROKARYOTIC SPECIES

(75) Inventors: Knut Rudi, Vestby (NO); Heidi Cecilie Vebø, As (NO)

(73) Assignee: Genetic Analysis AS (NO)

( * ) Notice: Subject to any disclaimer, the term of this patent is extended or adjusted under 35 U.S.C. 154(b) by 954 days.

(21) Appl. No.: 12/938,704

(22) Filed: Nov. 3, 2010

(65) Prior Publication Data

US 2011/0104692 A1    May 5, 2011

(30) Foreign Application Priority Data

Nov. 3, 2009    (GB) .................................. 0919264.2

(51) Int. Cl.
*C12Q 1/68*    (2006.01)
*C12P 19/34*    (2006.01)

(52) U.S. Cl.
CPC ................ *C12Q 1/689* (2013.01); *C12Q 1/686* (2013.01)
USPC ........................................ 435/6.12; 435/91.2

(58) Field of Classification Search
USPC .................... 435/6.12, 91.2; 536/24.32, 24.33
See application file for complete search history.

(56) References Cited

U.S. PATENT DOCUMENTS

| | | | |
|---|---|---|---|
| 4,267,234 | A | 5/1981 | Rembaum |
| 4,267,235 | A | 5/1981 | Rembaum et al. |
| 4,552,812 | A | 11/1985 | Margel et al. |
| 4,677,138 | A | 6/1987 | Margel |
| 4,717,655 | A | 1/1988 | Fulwyler |
| 4,774,189 | A | 9/1988 | Schwartz |
| 5,073,498 | A | 12/1991 | Schwartz et al. |
| 5,194,300 | A | 3/1993 | Cheung |
| 5,326,692 | A | 7/1994 | Brinkley et al. |
| 5,573,909 | A | 11/1996 | Singer et al. |
| 5,716,855 | A | 2/1998 | Lerner et al. |
| 5,723,218 | A | 3/1998 | Haugland et al. |
| 5,786,219 | A | 7/1998 | Zhang et al. |
| 6,951,714 | B2 | 10/2005 | Giovannoni et al. |
| 7,267,816 | B2 | 9/2007 | Hovanec |
| 7,309,601 | B2 | 12/2007 | Perez Esteban et al. |
| 7,553,626 | B2 | 6/2009 | Oh et al. |
| 2009/0253121 | A1* | 10/2009 | Halpern ............................ 435/5 |
| 2009/0263809 | A1 | 10/2009 | Roberton et al. |
| 2009/0263887 | A1 | 10/2009 | Keeler et al. |

FOREIGN PATENT DOCUMENTS

| | | |
|---|---|---|
| EP | 1920781 A1 | 5/2008 |
| WO | 9714028 A2 | 4/1997 |
| WO | 9851693 | 11/1998 |
| WO | 9919515 A1 | 4/1999 |
| WO | 9950448 A2 | 10/1999 |
| WO | 0039587 A1 | 7/2000 |
| WO | 0113119 A1 | 2/2001 |
| WO | 0113120 A1 | 2/2001 |
| WO | 0118524 A2 | 3/2001 |
| WO | 0153525 A2 | 7/2001 |
| WO | 0159432 A2 | 8/2001 |
| WO | 0200336 A2 | 1/2002 |
| WO | 0210444 A1 | 2/2002 |
| WO | 2004067738 A2 | 8/2004 |
| WO | 2009123736 A8 | 10/2009 |
| WO | 2010036876 A2 | 4/2010 |
| WO | 2010096514 A2 | 8/2010 |
| WO | 2010096515 A1 | 8/2010 |
| WO | 2010096537 A1 | 8/2010 |

OTHER PUBLICATIONS

Baker, et al.; "Review and Re-Analysis of Domain-Specific 16S Primers"; Journal of Microbiological Methods 55; pp. 541-555; (2003).

Neefs, et al.; "Compilation of Small Ribosomal Subunit RNA Sequences"; Nucleic Acids Research; 18 Supplement; pp. 2237-2318; (1990).

Syvanen, et al.; "A Primer-Guided Nucleotide Incorporation Assay in the Genotyping of Apolipoprotein E"; Genomics; 8; pp. 684-692; (1990).

Patent Act 1977: Search Report Under Section 17(5) & Opinion; Application No: GB0919264.2; Date of Search Jan. 19, 2010; 2 pages.

Weisburg, et al.; "16S Ribosomal DNA Amplification for Phylogenetic Study"; Journal of Bacteriology; 173; pp. 697-703; (1991).

* cited by examiner

*Primary Examiner* — Kenneth Horlick
(74) *Attorney, Agent, or Firm* — Cantor Colburn LLP

(57) ABSTRACT

Disclosed herein is a method of amplifying a target nucleotide sequence in 16S rRNA or in 16S rDNA that includes (a) contacting a sample that includes a 16S rDNA and/or the reverse transcription product of a 16S rRNA with an oligonucleotide primer having the nucleotide sequence of TCC TAC GGG AGG CAG CAG (SEQ ID NO 1) and an oligonucleotide primer comprising the nucleotide sequence of CGG TTA CCT TGT TAC GAC TT (SEQ ID NO 2); and (b) performing a primer-dependent nucleic acid amplification reaction to amplify the target nucleotide sequence in the 16S rRNA or the 16S rDNA. Also included are methods of measuring the prokaryotic content of a sample and/or determining the taxonomic classification of a prokaryotic organism in a sample by detecting and/or analyzing the amplification product.

17 Claims, 5 Drawing Sheets

```
                       SEQUENCE LISTING

<160> NUMBER OF SEQ ID NOS: 16

<210> SEQ ID NO 1
<211> LENGTH: 18
<212> TYPE: DNA
<213> ORGANISM: Artificial
<220> FEATURE:
<223> OTHER INFORMATION: Primer

<400> SEQUENCE: 1
tcctacggga ggcagcag                                                 18

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2 cggttaccttt gttacgactt                                              20

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
aagagtttga tcatggctca                                               20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
aagagtttga tcatggctca                                               20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5 cggttaccttt gttacgactt                                              20

<210> SEQ ID NO 6
<211> LENGTH: 17
<212> TYPE: DNA
<213> ORGANISM: Artificial
<220> FEATURE:
<223> OTHER INFORMATION: Primer

<400> SEQUENCE: 6
```

```
gagagtttga tcgctca                                                    17

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
aagagtttga tcctggctca                                                 20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
gagggttcga ttgtcgctca                                                 20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
agagtttgat cctggctcag                                                 20

<210> SEQ ID NO 10
<211> LENGTH: 19
<212> TYPE: DNA
<213> ORGANISM: Artificial
<220> FEATURE:
<223> OTHER INFORMATION: Primer

<400> SEQUENCE: 10
ggttaccttg ttacgactt                                                  19

<210> SEQ ID NO 11
<211> LENGTH: 15
<212> TYPE: DNA
<213> ORGANISM: Artificial
<220> FEATURE:
<223> OTHER INFORMATION: Primer

<400> SEQUENCE: 11
agagtttgat cctgg                                                      15

<210> SEQ ID NO 12
<211> LENGTH: 15
<212> TYPE: DNA
<213> ORGANISM: Artificial
<220> FEATURE:
<223> OTHER INFORMATION: Primer

<400> SEQUENCE: 12
aaaggaggtg atcca                                                      15

<210> SEQ ID NO 13
<211> LENGTH: 24
<212> TYPE: DNA
```

```
<213> ORGANISM: Artificial
<220> FEATURE:
<223> OTHER INFORMATION: Primer

<400> SEQUENCE: 13
cggtgtgtac aaggcccggg aacg                                          24

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
agagtttgat cmtggctcag                                               20

<210> SEQ ID NO 15
<211> LENGTH: 18
<212> TYPE: DNA
<213> ORGANISM: Artificial
<220> FEATURE:
<223> OTHER INFORMATION: Complementary sequence to SEQ ID NO 1

<400> SEQUENCE: 15
ctgctgcctc ccgtagga                                                 18

<210> SEQ ID NO 16
<211> LENGTH: 20
<212> TYPE: DNA
<213> ORGANISM: Artificial
<220> FEATURE:
<223> OTHER INFORMATION: Complementary sequence to SEQ ID NO 2

<400> SEQUENCE: 16
aagtcgtaac aaggtaaccg                                               20
```

METHODS OF AMPLIFYING A TARGET SEQUENCE OF A 16S RRNA OR 16S RDNA IN A PROKARYOTIC SPECIES

CROSS-REFERENCE TO RELATED APPLICATIONS

This application claims priority to GB0919264.2, filed Nov. 3, 2009, incorporated herein by reference in it entirety.

FIELD OF THE DISCLOSURE

The present disclosure relates to an oligonucleotide primer pair that permits the universal amplification of 16S rRNA or 16S rDNA present in a sample, and through which information on the distribution of the prokaryotic species in the sample may be obtained. This primer pair may be used to amplify 16S rRNA or 16S rDNA present in a sample in order to determine directly the total amount of prokaryotic cells, in particular bacteria, in a sample. This primer pair may also be used to amplify 16S rRNA or 16S rDNA present in a sample as a preliminary step in methods to determine the total amount of prokaryotic cells in a sample, or in methods to quantify, identify or classify specific prokaryotes, or types of prokaryotes, in a sample. The disclosure also provides kits comprising the primer pair and a complex comprising the primer pair hybridised to their complementary nucleotide sequences in a 16S rRNA or fragment thereof or a 16S rDNA or fragment thereof.

BACKGROUND

Information on the quantity of microorganisms present in a sample and information on the identity of the microorganisms in a sample is often essential in many technical fields, e.g. medicine, agriculture, veterinary science, environmental science and geological exploration, to enable informed decisions to be made.

Techniques for obtaining this information based on the culture of microorganisms are time consuming and often limited in terms of accuracy and practicality due to the potentially unknown and very varied conditions required to effect in vitro growth of the microorganisms in a particular sample.

A more promising approach uses the powerful techniques developed to amplify nucleic acids to characterise the microorganism content of samples, e.g. the polymerase chain reaction (PCR), the ligase amplification reaction (LAR), also known as ligase chain reaction (LCR), and strand displacement amplification (SDA). These methods are sensitive as the techniques used can produce results with only a few copies of the target nucleic acid. They are relatively inexpensive as sample size can be kept to a minimum and the necessary reagents and equipment are now relatively standard, small in size, readily available and cheap. Moreover, the degree of skill required to run these methods is also relatively low. In methods which seek to measure the total amount of microorganisms in a sample, or those that involve a step to amplify the microorganism derived nucleic acid before detection (quantitative or otherwise), a major concern is that the amplification techniques do not universally amplify nucleic acid from the microorganisms in a sample. Any bias against a microorganism will negatively impact any quantification of the total microorganism load of the sample and can provide a false negative in tests to identify, or classify, the type of microorganisms present in the sample.

The present disclosure addresses these problems by providing a primer pair that can permit the amplification of a region of nucleic acid from all, or at least substantially all, prokaryotic cells.

SUMMARY

In one aspect, a method of amplifying a target nucleotide sequence in 16S rRNA or in 16S rDNA comprises
(a) contacting a sample comprising a 16S rDNA and/or the reverse transcription product of a 16S rRNA with an oligonucleotide primer comprising the nucleotide sequence of SEQ ID NO 1 or a nucleotide sequence capable of hybridising under high stringency conditions to the sequence complementary to SEQ ID NO 1 and an oligonucleotide primer comprising the nucleotide sequence of SEQ ID NO 2 or a nucleotide sequence capable of hybridising under high stringency conditions to the nucleotide sequence complementary to SEQ ID NO 2; and
(b) performing a primer-dependent nucleic acid amplification reaction to amplify the target nucleotide sequence in the 16S rRNA or the 16S rDNA.

In another aspect, a method for measuring the prokaryote content of a sample, comprises performing the method described above on said sample, and (c) detecting the amplification product of step (b).

In yet another aspect, a method for determining the taxonomic classification of a prokaryotic organism in a sample, comprises performing the method described above on said sample, and (c) analysing the amplification product of step (b) to detect the presence or absence of a nucleotide sequence characteristic of a prokaryotic organism belonging to a specific taxonomic grouping.

In a further aspect, A primer pair consists of (i) an isolated oligonucleotide comprising the nucleotide sequence of SEQ ID NO 1 or a nucleotide sequence capable of hybridising under high stringency conditions to the sequence complementary to SEQ ID NO 1; and (ii) an isolated oligonucleotide comprising the nucleotide sequence of SEQ ID NO 2 or a nucleotide sequence capable of hybridising under high stringency conditions to the sequence complementary to SEQ ID NO 2.

In yet another aspect, a complex comprises
(i) an oligonucleotide primer comprising the nucleotide sequence of SEQ ID NO 1 or a nucleotide sequence capable of hybridising under high stringency conditions to the sequence complementary to SEQ ID NO 1; and
(ii) an oligonucleotide primer comprising the nucleotide sequence of SEQ ID NO 2 or a nucleotide sequence capable of hybridising under high stringency conditions to the sequence complementary to SEQ ID NO 2;
both hybridised to a 16S rRNA or fragment thereof or 16S rDNA or a fragment thereof.

In another aspect, a kit comprises
(i) an oligonucleotide primer comprising the nucleotide sequence of SEQ ID NO 1 or a nucleotide sequence capable of hybridising under high stringency conditions to the sequence complementary to SEQ ID NO 1; and
(ii) an oligonucleotide primer comprising the nucleotide sequence of SEQ ID NO 2 or a nucleotide sequence capable of hybridising under high stringency conditions to the sequence complementary to SEQ ID NO 2.

(lanes 1 to 12) and a negative control (lane 13) with the KlenTaq DNA Polymerase and 16SKR8F and 16SU1510R primers have been resolved.

Figure 2:
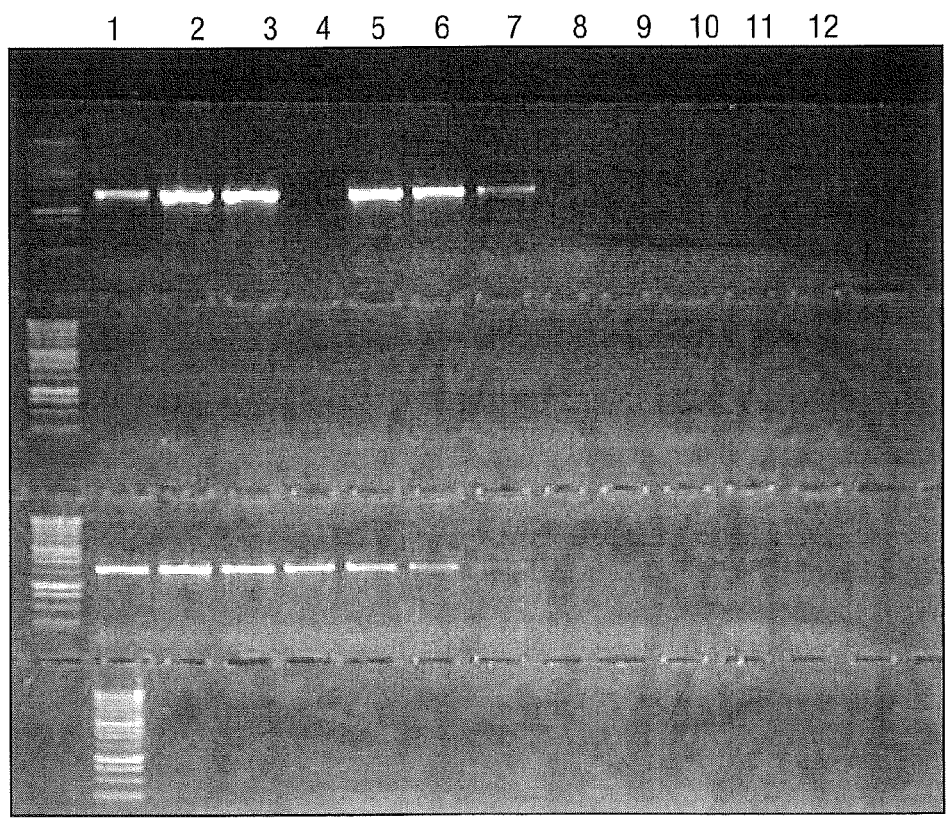

FIG. 2 is a photograph of a gel on which the products of a gradient PCR amplification of DNA from (A) *Bacterioides fragilis*; (B) *Bifidobacterium longum* spp *longum*; (C) *Escherichia coli*; (D) template-free negative control with the KR8F and U1510R primers (LNA) and Klentaq enzyme have been resolved. Lane/Temp (° C.): 1/55.1, 2/55.5, 3/56.3, 4/57.7, 5/59.4, 6/61.4, 7/63.3, 8/65.3, 9/67.6, 10/69, 11/69.7, 12/70.2.

Figure 3A:
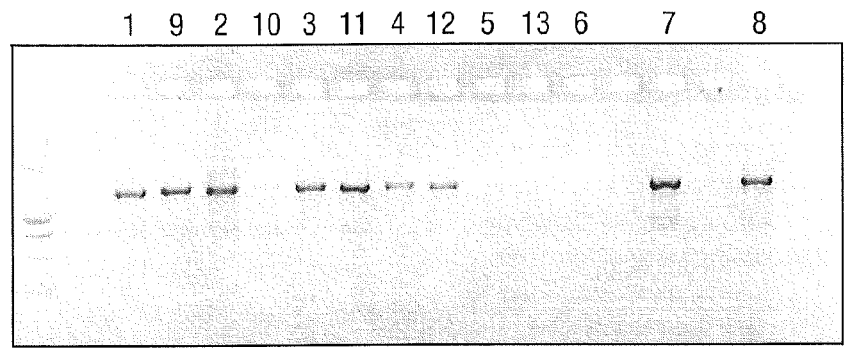
Figure 3B:
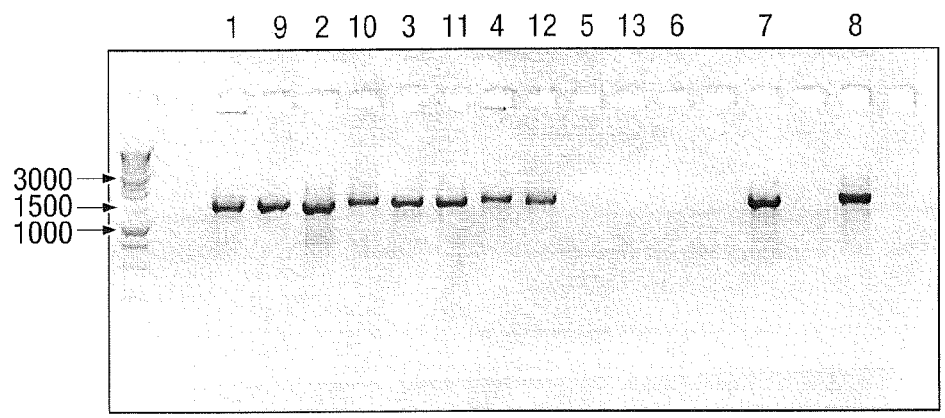
Figure 3C:
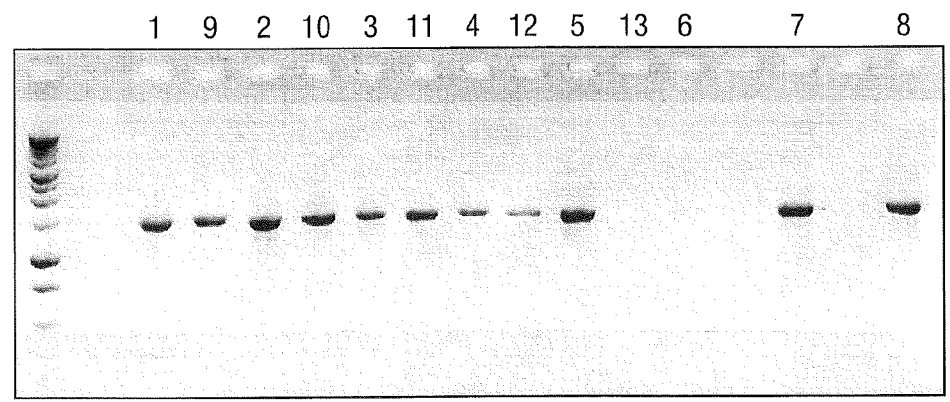
Figure 4:
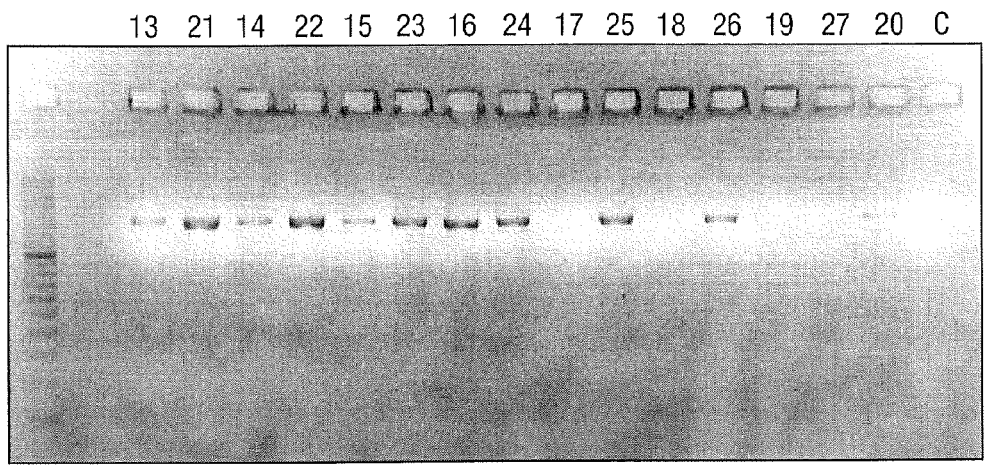

FIG. 3 is a photograph of a gel on which the products of the PCR amplification of DNA from sample numbers 1 to 12 (lanes 1 to 12) and a negative control (lane 13) with the KlenTaq DNA Polymerase and (A) 16S8FA and 16SU1510R primers; (B) 16S8FB and 16SU1510R primers; (C) 16S8FC and 16SU1510R primers have been resolved FIG. 4 is a photograph of a gel on which the products of the PCR amplification of DNA from sample numbers 13 to 27 (lanes 13 to 27) and negative control (lane C) with the KlenTaq DNA and the 16S8FC and 16SU1510R primer pair have been resolved.

Figure 5:
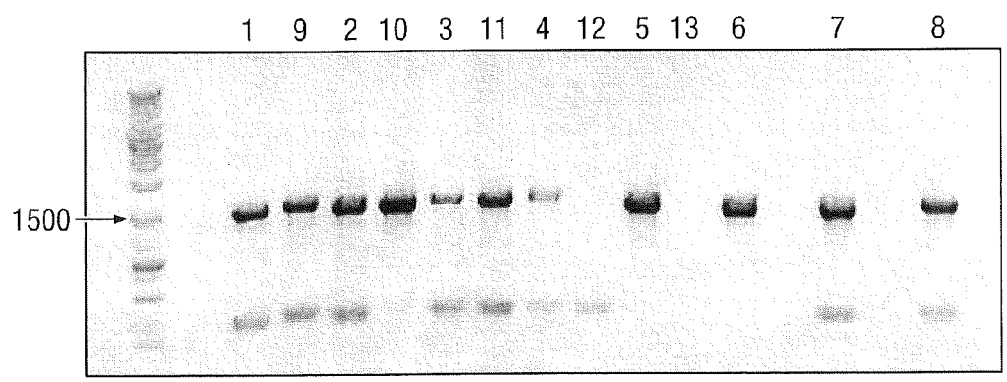

FIG. 5 is a photograph of a gel on which the products of the PCR amplification of DNA from sample numbers 1 to 12 (lanes 1 to 12) and a negative control (lane 13) with the KlenTaq DNA Polymerase and all of 16S8FA, 16S8FB, 16S8FC and 16SU1510R have been resolved.

Figure 6:
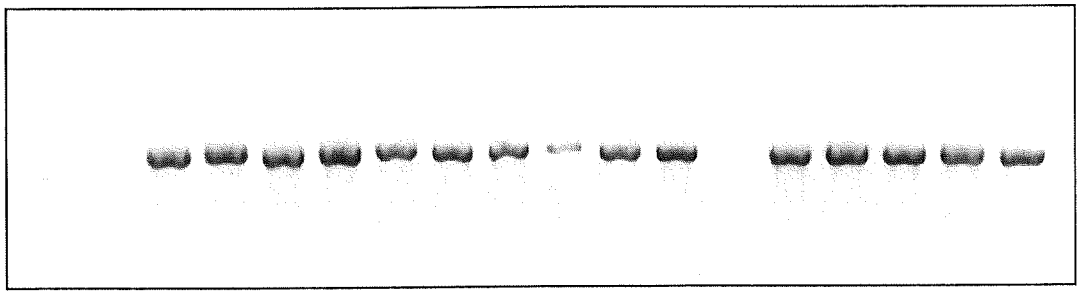
Figure 6:
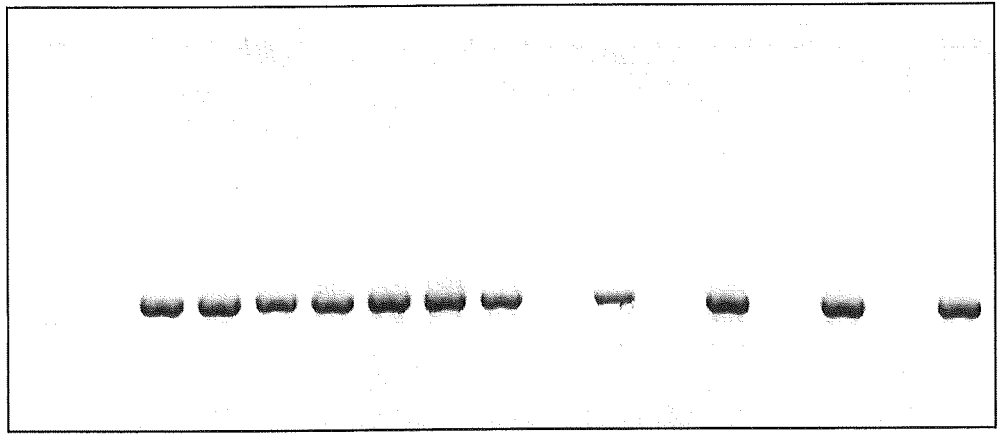

FIG. 6 is a photograph of a gel on which the products of the PCR amplification of DNA from sample numbers 1 to 27 (lanes 1 to 27) and negative control (lane C) with the KlenTaq DNA and the MangalaF-1 and 16SU1510R primer pair have been resolved.

Figure 7:
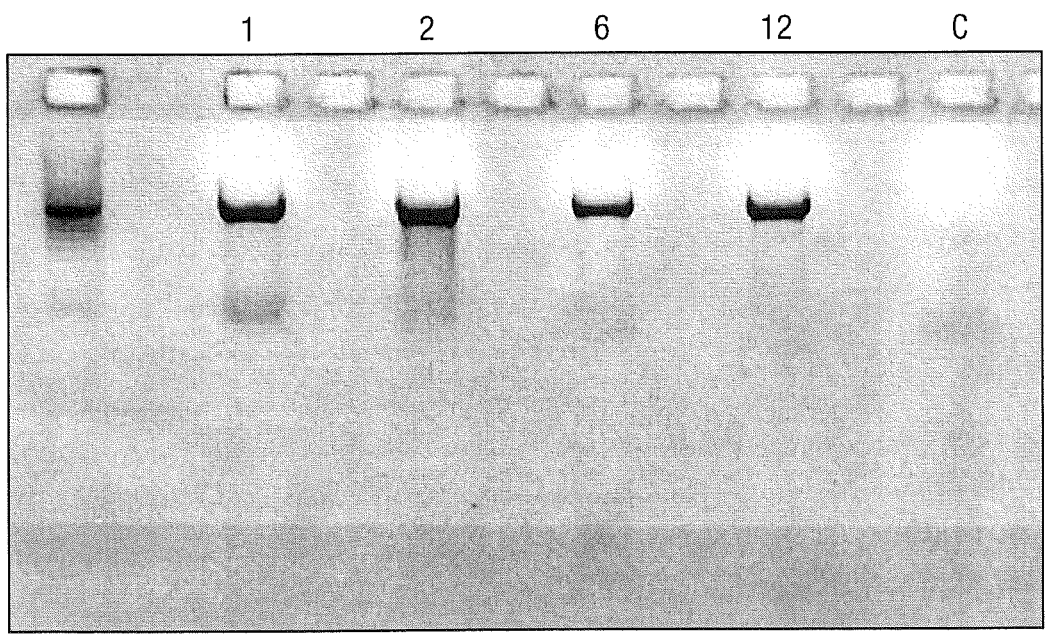

FIG. 7 is a photograph of a gel on which the products of the PCR amplification of DNA from sample 1, sample 2, sample 6 (*Bifidobacterium longum longum*) and sample 12 (*E. coli*) and negative control (lane C) with the KlenTaq DNA and the MangalaF-1 and 16SU1510R primer pair have been resolved

DETAILED DESCRIPTION

Described herein is a primer pair that can permit the amplification of a region of nucleic acid from all, or at least substantially all, prokaryotic cells. Thus, compared to known primer pairs, this primer pair permits a more accurate assessment of the amount of prokaryotic cells that might be in a sample and permits the unbiased amplification of nucleic acid from the prokaryotic cells in the sample thus providing a template for downstream analysis that is a substantially proportional representation of the initial sample.

Previous attempts to provide primers that may be used to provide for the universal amplification of prokaryotic nucleic acid have, inter alia, focused on 16S rRNA and its genes (rDNA), regions of which are highly conserved between prokaryotes, in particular the bacteria. However, as shown by the experiments described herein, not all pairings of these "universal" primers can in fact amplify 16S rRNA or 16S rDNA from all, or at least substantially all, prokaryotes, despite this being the intention behind their design. Indeed, the inventors have now shown that certain pairings are discriminatory in the amplification of 16S rRNA or 16S rDNA from different prokaryotes. The inventors have also identified a unique primer pair that amplifies a region of 16S rRNA or 16S rDNA with exceptional universality. One of the pair is a modified version of one of the primers described in WO02/10444 and the other is the same as that described in Baker, G. C., et al, J. Mic. Meth., 2003, Vol 55, 541-555 as U1510R. However, their use together has not been described before and the surprisingly high degree of universality has not been recognised or predicted before.

When investigating the prokaryote composition of a sample using techniques based on the amplification of 16S rRNA or 16S rDNA it may be advantageous to have an amplicon that is of sufficient length to include sequences characteristic of different prokaryotes or types of prokaryotes (thus permitting analysis of the amplification product). The longer the amplicon the greater the amount of sequence that is available to identify these characteristic sequences. This means that the optimal universal primer pair for the amplification of 16S rRNA or 16s rDNA not only has the greatest universality but also amplifies the longest amplicon. This combination of high universality and sufficient amplicon length is hard to achieve because the longer the amplicon, the smaller the region from which universal primer binding sites may be selected. However, the primer pair of the invention has exceptional universality and the amplicon will correspond to most of the sequence of the full length 16S rRNA of an prokaryote or the corresponding gene.

Thus, in a first aspect there is provided a method of amplifying a target nucleotide sequence in 16S rRNA or in 16S rDNA, said method comprising using (i) an oligonucleotide primer comprising the nucleotide sequence of SEQ ID NO 1 or a nucleotide sequence capable of hybridising under high stringency conditions to the sequence complementary to SEQ ID NO 1; and (ii) an oligonucleotide primer comprising the nucleotide sequence of SEQ ID NO 2 or a nucleotide sequence capable of hybridising under high stringency conditions to the nucleotide sequence complementary to SEQ ID NO 2 in a primer-dependent nucleic acid amplification reaction.

In this aspect said method of amplifying a target nucleotide sequence in 16S rRNA or in 16S rDNA comprises contacting a sample comprising a 16S rDNA and/or the reverse transcription product of a 16S rRNA with an oligonucleotide primer comprising the nucleotide sequence of SEQ ID NO 1 or a nucleotide sequence capable of hybridising under high stringency conditions to the sequence complementary to SEQ ID NO 1 and an oligonucleotide primer comprising the nucleotide sequence of SEQ ID NO 2 or a nucleotide sequence capable of hybridising under high stringency conditions to the nucleotide sequence complementary to SEQ ID NO 2 and performing a primer-dependent nucleic acid amplification reaction to amplify a target nucleotide sequence in the 16S rRNA or the 16S rDNA.

The amplification reaction is allowed to proceed for a duration (e.g. number of cycles) and under conditions that generate a sufficient amount of amplification product. A sufficient amount of amplification product will vary depending on the use to which the amplification product is put. The skilled man would readily be able to determine what amounts of amplification product he requires and the conditions and duration of the amplification reaction that would provide this amount.

In the following, references to "the nucleotide sequence of SEQ ID NO 1" or "the nucleotide sequence of SEQ ID NO 2" also include nucleotide sequences capable of hybridising under high stringency conditions to the sequence complementary to SEQ ID NO 1 or the nucleotide sequence complementary to SEQ ID NO 2, respectively, unless the context dictates otherwise.

A key component of all ribosomes is rRNA. In prokaryotes there are typically three rRNA molecules in a ribosome; the 5S and 23S in the large ribosome subunit and the 16S in the small ribosome subunit. Regions within the 16S rRNA, and therefore the genes encoding 16S rRNA, are highly conserved amongst prokaryotes, in particular amongst the bacteria.

In prokaryotes rRNA genes (which term is used herein interchangeably with the term rDNA) do not contain introns and so one strand of the rRNA gene will contain a nucleotide sequence that is the same as the nucleotide sequence of the rRNA and the other strand will contain the complementary nucleotide sequence of the rRNA nucleotide sequence.

The target nucleotide sequence amplified by the primers of the invention is therefore present in 16S rRNA and the corresponding 16S rRNA gene (rDNA). Thus, reference to the amplification of the target nucleotide sequence is a reference to an increase in the number of nucleic acids that contain that sequence of nucleotides without limitation on the type of nucleic acids containing the nucleotide sequence. Therefore these nucleic acids can be any nucleic acid, e.g. DNA, RNA, modifications thereof (e.g. PNA (peptide nucleic acids), morpholino-, LNA (locked nucleic acid)) and mixtures thereof. These nucleic acids may also be in single, double or multiple strand forms; which encompasses states in which the nucleic acid molecules are linear, are circular or have hybridised internally at one or more points. The multi-stranded forms can be heterogeneous, e.g. one strand is DNA and another is RNA. Typically, however, the nucleic acid that is formed as the amplification product is DNA, although the nucleotide sequence contained in that nucleic acid will still be the same as that of the target nucleotide sequence, or the complement thereof.

Conveniently, the method disclosed herein will be performed with 16S rDNA, e.g. a 16S rRNA gene, as the template. Typically, the sample comprising the 16S rDNA template will be a sample comprising a preparation of total bacterial DNA.

In other embodiments 16S rRNA may be the source of the target nucleotide sequence. When a target nucleotide sequence from 16S rRNA is amplified in the method of the invention there will be a step in which an RNA-dependent DNA polymerase catalyses the formation of a DNA molecule complementary to the 16S rRNA template (cDNA). This process is termed "reverse transcription". More specifically the RNA-dependent DNA polymerase catalyses the polymerisation of deoxyribonucleoside triphosphates in a sequence that is complementary (i.e. following Watson-Crick base pairing rules) to a primed template rRNA sequence.

Numerous enzymes have been identified that have the ability to catalyse this reaction and examples include, but are not limited to, HIV reverse transcriptase, AMV reverse transcriptase, M-MLV reverse transcriptase, *C. therm.* polymerase, and Tth polymerase. At its most basic a complete reverse transcription reaction mixture will contain a reverse transcription enzyme, the rRNA template, suitable primers that can bind to the template and from which the reverse transcriptase can begin polymerisation, dNTP's and a suitable buffer. Incubation of the mixture at the working temperature of the reverse transcriptase results in cDNA production.

Upon completion of the reverse transcription reaction the cDNA can be used as the template in the method of the invention described above. The cDNA therefore has a nucleotide sequence that is complementary to the rRNA molecule that was its template. In addition the cDNA has a nucleotide sequence that is the same as a nucleotide sequence contained in one strand of the gene of the rRNA template and the cDNA is complementary to a nucleotide sequence contained in the other strand of the gene of the rRNA template.

The target nucleotide sequence is a sequence of nucleotides in a 16S rDNA or a 16S rRNA that is amplified when the oligonucleotide primers disclosed herein are used as the forward and reverse primers of a primer-dependent amplification reaction in which the 16S rDNA or the reverse transcription product of the 16S rRNA is the template. Put in a different way, the target nucleotide sequence is that sequence of nucleotides in a 16S rDNA or a 16S rRNA that is found between the two oligonucleotide primers of the invention when said primers are hybridised, preferably under high stringency conditions, to the 16S rDNA, or the reverse transcription product of the 16S rRNA, as the forward and reverse primers of a primer-dependent amplification reaction. The target nucleotide sequence can be referred to as a "region of 16S rRNA or 16S rDNA"

The exact nucleotide sequence of the target nucleotide sequence will vary between prokaryotic organisms and these variations can be exploited to allow identification of the prokaryotic organisms from which the 16S rRNA or the 16S rDNA is derived. The target nucleotide sequence will typically correspond to the majority, or most, of the sequence of the full length 16S rRNA of a prokaryote or the corresponding gene. Typically this will comprise some or all, e.g. the main, hypervariable regions of 16S rRNA (e.g. V3 to V9). These regions are well characterised and defined in many prokaryotes (Neefs, J-M, et al, Nuc. Acid Res., Vol 18 Suppl., 2237-2317) and sequence alignment techniques can be used to identify these regions in any prokaryote 16S rRNA or the corresponding gene.

The oligonucleotide primers may comprise up to 100 nucleotides, preferably up to 80, 60, 50, 40, 30, 25, 24, 23, 22, 21, 20, 19 or up to 18 nucleotides. The oligonucleotide primers may comprise at least 15, preferably at least 16, 17, 18, 19, 20, 21, 22, 23, 24, 25, 30, 40, 60, or at least 80 nucleotides. The nucleotides of the oligonucleotide can be any type of nucleotide so long as hybridisation specificity or efficiency and amplification efficiency is not detrimentally effected. The oligonucleotide may therefore be a deoxyribonucleotide, a ribonucleotide, modifications thereof (e.g. PNA, morpholino-, LNA) and mixtures thereof DNA oligonucleotides and LNA modified DNA oligonucleotides are preferred.

The nucleotide sequence of SEQ ID NO 1 or SEQ ID NO 2 may be found in any part of the oligonucleotide primer so long as the primer can effect amplification of the target nucleotide sequence. In preferred embodiments the 3' nucleotide of SEQ ID NO 1 or SEQ ID NO 2 is the 3' nucleotide of the oligonucleotide primer.

In other embodiments the oligonucleotide primers consist essentially of SEQ ID NO 1 or SEQ ID NO 2. Thus the primer will have a nucleotide sequence corresponding to SEQ ID NO 1 or SEQ ID NO 2 and 1, 2, 3, 4, or 5 additional nucleotides. In other embodiments the oligonucleotide primers will consist of SEQ ID NO 1 or SEQ ID NO 2.

SEQ ID NO 1, also referred to herein as MangalaF-1, has the sequence TCC TAC GGG AGG CAG CAG and is capable of functioning as a forward primer in a primer dependent nucleic acid amplification reaction when used in combination with SEQ ID NO 2.

SEQ ID NO 2, also referred to herein as 16SU1510R, has the sequence CGG TTA CCT TGT TAC GAC TT and is capable of functioning as a reverse primer in a primer dependent nucleic acid amplification reaction when used in combination with SEQ ID NO 1.

The nucleotide sequence complementary to SEQ ID NO 1 is therefore CTG CTG CCT CCC GTA GGA (SEQ ID NO 15).

The nucleotide sequence complementary to SEQ ID NO 2 is therefore AA GTC GTA ACA AGG TAA CCG (SEQ ID NO 16).

Unless otherwise stated, or dictated by specific context, all nucleotide sequences are recited herein 5' to 3' in line with convention in this technical field.

The oligonucleotide primers may be labelled with a moiety to assist with detection or manipulation. A large number of suitable moieties and labelling methods are known in the art and described in the literature. Many moieties can perform both functions. Any detectable or signal-generating molecule or reporter molecule may be used. Convenient labels include colorimetric, chemiluminescent, chromogenic, radioactive and fluorescent labels, but enzymatic (e.g. colorimetric, luminescent, chromogenic) or antibody-based labelling methods or signal-generating systems may also be used. Thus the term "label" as used herein includes not only directly detectable signal-giving or passive moieties, but also any moiety which generates a signal or takes part in a signal generating reaction or that may be detected indirectly in some way.

The label can, in some embodiments, comprise a plurality of moieties that contributes to the overall detectable output of the label. By varying the identity and/or the relative proportions of these moieties, a wide palette of unique labels can be constructed. For instance, a plurality of dyes, e.g. luminescent (e.g. bioluminescent, chemiluminescent, photoluminescent, radioluminescent, sonoluminescent, etc.) which combine to give a unique electromagnetic spectral signature upon excitation may be used. By varying the proportions of the selected dyes further differentiation in the spectral signature can be achieved. Signatures based on the absorption of certain wavelengths of electromagnetic radiation are also envisaged.

Fluorescein or other fluorescently labelled nucleotides are particularly suitable for incorporation into the primers, and allow detection directly by fluorescence or indirectly by antibody interactions. These are commercially available. Primers can be labelled by e.g. [$^{35}$S], [$^{3}$H] or [$^{32}$P] as described in Syvänen, A. C. et al. Genomics 8, [1990], 684-692. Any binding moiety may be used, for instance an antibody fragment, His-tag, biotin or streptavidin.

The oligonucleotide primers can also be provided, or be, immobilised on solid supports for use in the invention. Suitable immobilising supports to which the oligonucleotide primers can be attached are known in the art and include any of the well known supports or matrices which are currently widely used or proposed for immobilisation, separation etc. of oligonucleotides. These may take the form of particles, sheets, gels, filters, membranes, fibres, capillaries, chips or microtitre strips, slides, tubes, plates or wells etc. Methods of immobilising or attaching oligonucleotides to solid supports are likewise known in the art. Particularly preferred are membrane strips on to which the primers may be spotted and then UV cross-liked, or DNA chips (microchips, glass chips) now common in molecular biology procedures.

Also particularly preferred are particles, e.g. beads on to which the primers have been attached. In certain embodiments the particles also carry a label to permit their detection. Suitable particles are described in more detail later.

Preferably the support is magnetic, e.g. magnetic particles, for instance magnetic beads.

In certain embodiments the methods of the invention are performed with one or both oligonucleotides immobilised on a solid support with the other oligonucleotide primer of the pair being provided in solution. In other embodiments none of the primers are used in the method of the invention in immobilised form.

High stringency conditions for hybridisation are defined as 2×SSC/50% formamide at 50° C. for binding conditions and 2×SSC at 65° C. for washing conditions (where SSC=0.15 M NaCl, 0.015 M sodium citrate, pH 7.2).

In preferred embodiments the nucleotide sequences that can hybridise to the nucleotide sequence complementary to SEQ ID NO. 1 under high stringency conditions will hybridise to all, or substantially all, e.g. at least 10, 11, 12, 13, 14, 15, 16, or 17 contiguous nucleotides of the nucleotide sequence complementary to SEQ ID NO. 1 (i.e. SEQ ID NO 15).

In preferred embodiments the nucleotide sequences that can hybridise to the nucleotide sequence complementary to SEQ ID NO. 2 under high stringency conditions will hybridise to all, or substantially all, e.g. at least 10, 11, 12, 13, 14, 15, 16, 17, 18 or 19 contiguous nucleotides of the nucleotide sequence complementary to SEQ ID NO. 2 (i.e. SEQ ID NO 16).

Viewed alternatively, nucleotide sequences that can hybridise to the nucleotide sequences complementary to SEQ ID NO. 1 or SEQ ID NO. 2 under high stringency conditions may be those nucleotide sequences that correspond to the nucleotide sequence of SEQ ID NO. 1 or SEQ ID NO. 2 but with up to 8 bases (adenine, thymine/uracil, guanine, or cytosine) in the nucleotide sequences of SEQ ID NO. 1 or SEQ ID NO. 2 being substituted with a different base. Preferably there will be up to 7, 6, 5, 4, 3 or 2 substituted bases or only a single base substitution. The base being substituted into the sequence can be any standard or non-standard, naturally occurring or synthetic base. Nucleotide sequences that can hybridise to the nucleotide sequence complementary to SEQ ID NO. 1 under high stringency conditions will preferably be 15, 16, 17 or 18 nucleotides in length, and consist of a contiguous part of the nucleotide sequence of SEQ ID NO. 1 with the above described substitutions. Nucleotide sequences that can hybridise to the nucleotide sequence complementary to SEQ ID NO. 2 under high stringency conditions will preferably be 17, 18, 19 or 20 nucleotides in length, consist of a contiguous part of the nucleotide sequence of SEQ ID NO 2 with the above described substitutions.

Preferably the base substitution(s) occur at or near the 5' end of the nucleotide sequence, e.g. in the final 15, 10 or 5 5' nucleotides in the sequence. Put differently, the base substitution(s) preferably do not occur at or near the 3' end of the nucleotide sequence, e.g. in the final 2, 3, 4, 5, 10 or 15 3' nucleotides. In other embodiments the 3' nucleotide will not have a substituted base.

As mentioned above, the primer pair permits the amplification of a region of 16S rRNA or 16S rDNA from all, or at least substantially all, prokaryotic cells, e.g. those that might be present in a sample. The term "amplification from substantially all prokaryotic cells present in a sample" refers to the number of different species of prokaryotic cells in the sample that the primers of the invention are capable of amplifying. Thus, the primer pair of the invention is capable of amplifying nucleic acid from at least one representative of substantially all species of prokaryotic cells in a sample (e.g. at least 80, 90, 95, 98, or 99% of the different prokaryotic species that might be in a sample). In certain embodiments the species *Alcaligenes faecalis, Bacillus alcalophilus* (13012010), *Bacterioides caccae, Collinsella* sp., *Corynebact. aurimucosum, Corynebact. glucuronolyticum, Corynebact. lipophiloflavum, Corynebacterium jeikeium* (15012010), *Corynebacterium striatum, Collinsella aerofaciens, Mycobact. parascrofulaceum, Parascardovia denticolens, Streptomyces albus*, and *Streptomyces lanatus* are excluded from the calculation of these values. In other embodiments bacteria from the genera *Alcaligenes, Bacillus, Bacterioides, Collinsella, Corynebacterium, Mycobacterium, Parascardovia* and *Streptomyces* are excluded from the calculation of these values. The term "substantially all prokaryotic cells" refers to at least 80, 90, 95, 98, or 99% of prokaryotic species, not including, in certain embodiments, the species *Alcaligenes faecalis, Bacillus alcalophilus* (13012010), *Bacterioides caccae, Collinsella* sp., *Corynebact. aurimucosum, Corynebact. glucuronolyticum, Corynebact. lipophiloflavum, Corynebacterium jeikeium* (15012010), *Corynebacterium striatum, Collinsella aerofaciens, Mycobact. parascrofulaceum, Parascardovia denticolens, Streptomyces albus,* and *Streptomyces lanatus* or, in other embodiments, bacteria from the genera *Alcaligenes, Bacillus, Bacterioides, Collinsella, Corynebacterium, Mycobacterium, Parascardovia* and *Streptomyces*. The term "substantially all bacterial cells" should be construed in the same way.

By "prokaryotic cell" it is meant any organism that lacks a cell nucleus, i.e. any organism from the domains Bacteria and Archaea. Preferably the prokaryotic cell is a bacterium.

Representative examples of Archaea divisions are Euryarchaeota, Crenarchaeota, Thaumarchaeota, Korarchaeota and Nanoarchaeota. Preferably the prokaryotic cell is an Archea prokaryote from the divisions Euryarchaeota or Crenarchaeota. Representative orders of Archea include, but are not limited to, Sulfolobales, Thermoproteales, Desulfurococcales, Archaeaglobales, Halobacteriales, Methanococcales, Thermococcales. Representative Archaea genera include, but are not limited to, *Aeropyrum, Halobacterium, Halorubrum, Methanobrevibacter, Methanosarcina, Nanoarchaeum, Pyrococcus, Pyrolobus, Thermococcus, Thermococcus litoralis*. Representative Archaea species include, but are not limited to, *Aeropyrum pernix, Halobacterium salinarum, Halorubrum salsolis, Methanobrevibacter smithii, Methanosarcina acetivorans, Nanoarchaeum equitans, Pyrococcus furiosus, Pyrolobus fumarii, Thermococcus celer, Thermococcus litoralis*.

Examples of genera or species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*; e.g. gram-positive bacteria such as *Clostridium tetani, Clostridium perfringens, Clostridium botulinum, M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, Actinomyces israelii, Propionibacterium acnes,* and *Enterococcus* species and Gram-negative bacteria such as *Pseudomonas aeruginosa, Vibrio cholerae, Actinobacillus pleuropneumoniae, Pasteurella haemolytica, Pasteurella multocida, Legionella pneumophila, Salmonella typhi, Brucella abortus, Chlamydia trachomatis, Chlamydia psittaci, Coxiella burnetti, Escherichia coli, Neiserria meningitidis, Neiserria gonorrhea, Haemophilus influenzae, Haemophilus ducreyi, Yersinia pestis, Yersinia enterolitica, Escherichia hirae, Burkholderia cepacia, Burkholderia pseudomallei, Francisella tularensis, Bacteroides fragilis, Fusobascterium nucleatum, Cowdria ruminantium, Moraxella catarrhalis, Klebsiella pneumoniae, Proteus mirabilis, Enterobacter cloacae, Serratia marcescens, Helicobacter pylori, Salmonella enteritidis, Salmonella typhi* and *Acinetobacter baumaneii*. Further examples are recited in Tables 1, 9 and 11.

In other embodiments the primer pair disclosed herein can amplify a target nucleotide sequence in the 16S rRNA and 16S rDNA from substantially all, or all, e.g. at least 90%, preferably at least 95, 97, 98, 99 or 100% of the following prokaryotes: *Acidsminococcus intestini, Acinetobacter baumannii, Acinetobacter junii, Acinetobacter* sp., *Actinomyces cardiffensis, Actinomyces urogenitalis, Aeromicrobium marinum, Aeromonas hydrophila ss hydro, Aeromonas sobria, Akkersmania municiphila, Alistipes putredinis, Alistipes shahii, Anaerobaculum mobile, Anaerococcus hydrogenalis, Anaerococcus prevotii, Anaerofustis stercorihominis, Anaeroglobus geminatus, Anaerostipes caccae, Anaerotruncus colihominis, Aneurinibacillus aneurinilyticus, Atopobium rimae, Atopobium vaginae, Bacterioides dorei, Bacterioides fragilis, Bacterioides stercoris, Bacterioides thetaiotamicron, Bacterioides vulgatus, Bacteroides capillosus, Bacteroides cellulosilyticus, Bacteroides coprocola, Bacteroides coprophilus, Bacteroides eggerthii, Bacteroides finegoldii, Bacteroides galacturonicus, Bacteroides intestinalis, Bacteroides massiliensis, Bacteroides ovatus, Bacteroides plebeius, Bacteroides uniformis, Bacteroides xylanisolvens, Bifid. longum* subsp *longum, Bifid. longum* subsp. *infantis, Bifidobacterium adolescentis, Bifidobacterium angulatum, Bifidobacterium bifidum, Bifidobacterium breve, Bifidobacterium catenulatum, Bifidobacterium dentium, Bifidobacterium gallicum, Bifidobacterium pseudocatenulatum, Blautia coccoides, Blautia hansenii,*

*Brevibacterium mcbrellneri, Bryantella formatexigens, Bulleidia extructa, Burkholderia oklahomensis, Butyrivibrio crossotus, Butyrivibrio fibrisolvens, Campylobacter concisus, Campylobacter curvus, Campylobacter jejuni, Capnocytophaga gingivalisi, Capnocytophaga ochraceai, Capnocytophaga sputigenai, Catenibacterium mitsuokai, Cedecea davisae, Cetobacterium somerae, Chryseobacterium gleum, Citrobacter youngae, Clostridium algidixylanolyticum, Clostridium amygdalinum, Clostridium asparagiforme, Clostridium bartlettii, Clostridium bolteae, Clostridium celatum, Clostridium chauvoei, Clostridium difficile, Clostridium fimetarium, Clostridium glycyrrhizinilyticum, Clostridium hathewayi, Clostridium hiranonis, Clostridium histolyticum, Clostridium hylemonae, Clostridium indolis, Clostridium jejuense, Clostridium leptum, Clostridium methoxybenzovorans, Clostridium methylpentosum, Clostridium orbiscindens, Clostridium paraputrificum, Clostridium perfringens, Clostridium ramosum, Clostridium saccharolyticum, Clostridium scindens, Clostridium septicum, Clostridium sp., Clostridium sphenoides, Clostridium spiroforme, Clostridium sporogenes, Clostridium symbiosum, Clostridium xylanolyticum, Clostridium xylanovorans, Collinsella aerofaciens, Collinsella intestinalis, Coprococcus comes, Coprococcus eutactus, Delflia tsuruhatensis, Desulfitobacterium hafniense, Desulfomonas pigra, Desulfotomaculum guttoideum, Dialister invisus, Dorea longicatena, Edwardsiella tarda, Eggerthella lenta, Eikenella corrodens, Enterobacter aerogenes, Enterobacter cancerogenus, Enterobacter hormaechei, Enterobacter hormaechei oharae, Enterococcus faecalis, Enterococcus faecium, Erypeothrix rhusiopathiae, Escherichia albertii, Escherichia coli, Eubacterium biforme, Eubacterium cylindroides, Eubacterium dolichum, Eubacterium hallii, Eubacterium plautii, Eubacterium ramulus, Eubacterium rectale, Eubacterium siraeum, Faecalibacterium prausnitzii, Finegoldia magna, Fusobacterium gonidiaformans, Fusobacterium nucleatum, Fusobacterium periodonticum, Gardnerella vaginalis, Gemella bergeri, Gemella haemolysans, Gemella sanguinis, Gordonibacter pamelaeae, Granulicatella elegans, Hafnia alvei, Helicobacter canadensis, Helicobacter cinaedi, Helicobacter pylori, Hespellia porcina, Holdemania filiformis, Klebsiella oxytoca, Kleibsiella pneu, Labctobacillus sakei ssp. Carnosus, Lachno Blautia hydrogenotrophica, Lachno Blautia luti, Lachno Blautia schinkii, Lachno Clostridium aerotolerans, Lachno Clostridium celerecrescens, Lachno Clostridium clostridioforme, Lachno Clostridium colinum, Lachno Clostridium nexile, Lachno Clostridium populeti, Lachno Dorea formicigenerans, Lachno Eubacterium contortum, Lachno Eubacterium ventriosum, Lachno Pseudobutyrivibrio ruminis, Lachno Roseburia intestinalis, Lachno Sporobacterium olearium, Lachnobacterium bovis strain, Lacrobacillus rhamnosus, Lactobacillus brevis, Lactobacillus crispatus, Lactobacillus acidophilus, Lactobacillus amylolyticus, Lactobacillus antri, Lactobacillus buchneri, Lactobacillus casei, Lactobacillus coleoohomnis, Lactobacillus delbrueckii ssp bulgaricus, Lactobacillus fermentum, Lactobacillus gasseri, Lactobacillus helveticus, Lactobacillus hilgardii, Lactobacillus iners, Lactobacillus jensenii, Lactobacillus johnsonii, Lactobacillus paracasei, Lactobacillus plantarum, Lactobacillus reuteri, Lactobacillus ruminis, Lactobacillus salivarius, Lactobacillus ultunensis, Lactobacillus vaginalis, Laribacter hongkongensis, Leptotrichia goodfellowii, Leptotrichia hofstadii, Leptotrichia wadei, Leuconostoc mesenteroides ssp. Cremoris, Listeria grayi strain, Listeria innocua, Listeria monocytogenes, Megamonas hypermegale, Megasphaera micronuciformis, Methanobrevibacter smithii, Methanobrevibacter smithii, Methanosphaera stadtmanae, Mitsukoella multiacid, Mobiluncus curtisii, Mobiluncus mulieris, Morganella morganii, Mycoplasma hominis, Neisseria subflava, Oribacterium sinus, Parabacterioides distas, Parabacterioides merdae, Parabacteroides johnsonii, Parabacteroides merdae, Parasporobacterium paucivorans, Parvimonas micra, Pediococcus acidilactici, Pelomonas aquatica, Peptostreptococcus stomatis, Phascolarctobacterium faecium, Porphyromonas gingivalis, Porpyromonas endodontalis, Prevotella amnii, Prevotella copri, Prevotella marshii, Prevotella melaminogenica, Prevotella oralis, Prevotella oris, Prevotella stercorea, Prevotella timonensis, Prevotella veroralis, Proteus mirabilis, Proteus penneri, Proteus vulgaris, Providencia alcalifaciens, Providencia rettgeri, Providencia rustigianii, Providencia stuartii, Pseudomonas gessardii, Pseudoramibacter alactolyticus, Pyramidobacter piscolens, Ralstonia sp., Raoultella ornithinolytica, Rhodotrula mucilaginosa, Roseburia faecis, Roseburia inulinivorans, Roseomonas cervicalis, Rothia dentocariosa, Ruminococcus albus, Salmonella bongori, Salmonella ent, Salmonella enteritidis, Scardovia inopinata, Selenomonas noxia, Selenomonas sputigena, Serratia marcescens, Shigella dysenteriae, Shigella sonnei, Shuttleworthia satelles, Simonsiella muelleri, Slackia exigua, Sphingobacterium spiritivorum, Staph. aureus* subsp *aureus, Staphylococcus epidermidis, Stenotrophomonas maltophilia, Streptococcus infantarius, Streptococcus agalactiae, Streptococcus equinus, Streptococcus mitis, Streptococcus oralis, Streptococcus pneu, Streptococcus pyog, Streptococcus sang, Subdoligranulum variabile, Syntrophococcus sucromutans, Veillonella atypicon, Veillonella dispar, Veillonella parvula, Victivallis vadensis, Weissella paramesenteroides, Yersina bercovieri, Yersinia enterocolitica, Yersinia pestis, Yersinia pseudotuberculosis, Yokenella regensburgei, Campylobacter jejuni* subsp *jejuni, Haemophilus parainfl* and *Salmonella enterica* subsp. *enterica* or any bacteria from the genera listed in this paragraph. In this and other embodiments the primer pair of the invention will at least amplify a target nucleotide sequence in the 16S rRNA and 16S rDNA from one or more of *Aeromicrobium marinum, Aeromonas hydrophila ss hydro, Aneurinibacillus aneurinilyticus, Bacterioides fragilis, Bifid. longum* subsp *longum, Bifidobacterium breve, Bifidobacterium catenulatum, Bifidobacterium dentium, Bifidobacterium pseudocatenulatum, Clostridium chauvoei, Clostridium sphenoides, Desulfomonas pigra, Gardnerella vaginalis, Gordon ibacter pamelaeae, Lachno Clostridium aerotolerans, Lactobacillus fermentum, Laribacter hongkongensis, Methanosphaera stadtmanae, Proteus mirabilis, Rhodotrula mucilaginosa and Slackia exigua,* especially *Aeromicrobium marinum, Bacterioides fragilis, Clostridium chauvoei, Clostridium sphenoides, Gardnerella vaginalis, Laribacter hongkongensis, Proteus mirabilis, Rhodotrula mucilaginosa* and *Slackia exigua*

Amplification can be achieved by any convenient primer-dependent nucleic acid amplification reaction. Most conveniently the polymerase chain reaction (PCR) will be used, although the skilled man would be aware of other techniques. For instance LAR/LCR, SDA, Loop-mediated isothermal amplification and nucleic acid sequence based amplification (NASBA)/3SR (Self-Sustaining Sequence Replication) may be used.

Many variations of PCR have been developed, for instance Real Time PCR (also known as quantitative PCR, qPCR), hot-start PCR, competitive PCR, and so on, and these may all be employed where appropriate to the needs of the skilled man.

In one basic embodiment using a PCR based amplification the oligonucleotide primers of the invention are contacted with a reaction mixture containing the target sequence and free nucleotides in a suitable buffer. Thermal cycling of the resulting mixture in the presence of a DNA polymerase results in amplification of the sequence between the primers.

Optimal performance of the PCR process is influenced by choice of temperature, time at temperature, and length of time between temperatures for each step in the cycle. A typical cycling profile for PCR amplification is (a) 15 minutes of DNA melting at 95° C.; (b) 30 seconds of primer annealing at 50-65° C.; (c) 90 seconds of primer extending at 68-72° C.; (d) 30 seconds of DNA melting at 95° C.; and steps (b)-(d) are repeated as many times as necessary to obtain the desired level of amplification. In certain embodiments the annealing step is performed at 50-60° C., e.g. 50-58° C., 52-58° C., 53-57° C., or 53-55° C. In other embodiments the annealing step is performed at about 55° C. (e.g. 55° C.±3° C., 55° C.±2° C. 55° C.±1° C. or 55° C.±0.5° C.). The annealing step of other amplification reactions may also be performed at any of these temperatures.

As mentioned above, if 16S rRNA is used as the source of the target nucleotide sequence (as opposed to 16S rDNA, e.g. a 16S rRNA gene) an initial reverse transcription step is required. Reverse transcription linked amplification reactions, in particular PCR, can be "one step" or "two step" processes. In a one step process the components of the reverse transcription reaction and the nucleic acid amplification reaction are present in a single reaction vessel and typically the early reaction conditions are selected to allow the reverse transcription reaction to proceed to completion and reaction conditions are then switched to conditions suitable to allow the nucleic acid amplification reaction to proceed.

In a two step process the components of the reverse transcription reaction are first combined and the reverse transcription reaction is performed. The reverse transcription product is then combined with the components of the amplification reaction and subjected to the amplification reaction. In a "one tube" two step protocol the amplification reaction components are added to the same reaction vessel in which the reverse transcription reaction was performed. In a "two tube" two step protocol the amplification reaction is performed in a fresh reaction vessel. Typically, in these embodiments, the primers of the invention will make up a part of the components of the nucleic acid amplification reaction.

Modifications of the basic PCR method such as qPCR (Real Time PCR) have been developed that can provide quantitative information on the template being amplified. Numerous approaches have been taken although the two most common techniques use double-stranded DNA binding fluorescent dyes or selective fluorescent reporter probes.

Double-stranded DNA binding fluorescent dyes, for instance SYBR Green, associate with the amplification product as it is produced and when associated the dye fluoresces. Accordingly, by measuring fluorescence after every PCR cycle, the relative amount of amplification product can be monitored in real time. Through the use of internal standards and controls, this information can be translated into quantitative data on the amount of template at the start of the reaction.

The fluorescent reporter probes used in qPCR are sequence specific oligonucleotides, typically RNA or DNA, that have a fluorescent reporter molecule at one end and a quencher molecule at the other (e.g. the reporter molecule is at the 5' end and a quencher molecule at the 3' end or vice versa). The probe is designed so that the reporter is quenched by the quencher. The probe is also designed to hybridise selectively to particular regions of complementary sequence which might be in the template. If these regions are between the annealed PCR primers the polymerase, if it has exonuclease activity, will degrade (depolymerise) the bound probe as it extends the nascent nucleic acid chain it is polymerising. This will relieve the quenching and fluorescence will rise. Accordingly, by measuring fluorescence after every PCR cycle, the relative amount of amplification product can be monitored in real time. Through the use of internal standard and controls, this information can be translated into quantitative data.

As mentioned above, the primer pair of the invention permits the amplification of a region of 16S rRNA or 16S rDNA from all, or at least substantially all, prokaryotic cells, e.g. those that might be present in a sample. The amount of these nucleic acids in a sample will be proportional to the total prokaryote content in the sample and so the primers of the invention can be used to measure the total prokaryote content in a sample.

Thus, in another aspect, provided herein is a method for measuring the prokaryote content of a sample, said method comprising contacting a sample containing, or suspected of containing, prokaryotes with (i) an oligonucleotide primer comprising the nucleotide sequence of SEQ ID NO 1 or a nucleotide sequence capable of hybridising under high stringency conditions to the sequence complementary to SEQ ID NO 1; and (ii) an oligonucleotide primer comprising the nucleotide sequence of SEQ ID NO 2 or a nucleotide sequence capable of hybridising under high stringency conditions to the sequence complementary to SEQ ID NO 2 and performing a primer-dependent nucleic acid amplification reaction.

Detection of the product resulting from the primer-dependent nucleic acid amplification reaction thereby provides a measure of the prokaryote content of a sample.

In this aspect the primer-dependent nucleic acid amplification reaction amplifies a target nucleotide sequence in the 16S rRNA or in the 16S rDNA in a sample under conditions and for a duration that generates an amount of amplification product that is proportional to the amount of target nucleotide sequence in said sample immediately before the amplification reaction begins. Preferably the method includes steps in which the amount of amplification product is determined thereby providing a measure of the prokaryote content of a sample.

"Measuring the prokaryote content of a sample" refers to the assessment of the quantity of prokaryotic organisms that are in a sample. It does not require identification of the type of prokaryotic organisms in the sample. Nor does it necessarily provide a measure of the number of individual prokaryotic organisms in the sample, although this can be achieved if appropriate quantitative techniques are applied to the method. The measure may therefore be qualitative, semi quantitative or quantitative.

At its most basic, the method of this aspect can provide confirmation of the presence or absence of a prokaryotic cell in a sample (detection of any amplification product is sufficient to confirm the presence of a prokaryotic cell in the sample and absence of an amplification product is indicative of the absence of prokaryotic cells in the sample). The method also provides a relative measure of the prokaryote content of a sample in terms of the amount of amplification product obtained. This measurement can be compared with other samples which have undergone amplification with the same conditions to provide information on the relative prokaryote contents of those samples. In this way the relative effects of one or more changing parameters (e.g. time, temperature, nutrient concentration, toxin concentration) on prokaryote levels can be assessed simply and quickly.

The amplification product may be detected, and amounts of amplification product can be determined by a convenient means. A vast number of techniques are routinely employed as standard laboratory techniques and the literature has descriptions of more specialised approaches. At its most simple the amount of amplification product may be detected or determined by visual inspection of the reaction mixture at the end of the reaction or at a desired timepoint. Typically the amplification product will be resolved with the aid of a label that may be preferentially bound to the amplification product. Typically a dye substance, e.g. a colorimetric, chromomeric fluorescent or luminescent dye (for instance ethidium bromide or SYBR green) is used. In other embodiments a labelled oligonucleotide probe that preferentially binds the amplification product, in particular a probe that binds preferentially to substantially all of the individual amplified nucleic acids in the amplification product, is used. A suitable probe is disclosed in WO02/10444 and suitable labels for the probe are discussed above in relation to the oligonucleotide primers of the invention. In some embodiments the probe may be provided in an unlabelled form with labelling occurring after preferential binding to the amplification product, or preferential binding to substantially all of the individual amplified nucleic acids in the amplification product.

However, in some cases a nucleic acid precipitant (e.g. salt and/or alcohol) can simply be used to cause the amplification product to come out of solution and be visible without labelling.

To aid visualisation the components of amplification product can be dispersed in or on a solid support, for instance by electrophoresis (e.g. using agarose or polyacrylamide gels), chromatography (e.g. HPLC, TLC, affinity, gel filtration) or filtration, or a combination thereof, prior to or after contact with the label.

Depending on the label used detection can be made more accurate by using widely available detection technologies, e.g. radiation sensitive films and digital imaging technologies in combination with computer assisted image analysis, photometers, fluorometers, colorimeters, scintillation counters, and the like. With an accurate measure of the amount of amplification product, comparison to results from amplification products from samples of known prokaryote content or of known quantities of target nucleotide sequence allows quantification of the prokaryote content of the sample.

Preferably the amplification product is separated from the remainder of the amplification reaction before being contacted by the label, e.g. in the form of a labelled oligonucleotide probe. This may be by any convenient means, for instance with one or more washing steps (e.g. with water or a buffered solution which may contain formamide and/or a detergent), electrophoresis, centrifugation, capture onto nucleic acid binding solid supports, chromatography or any combination thereof. Conveniently, the probe can be provided on a solid support thereby effecting separation of the amplification product from the remainder of the amplification reaction in a single step. In another embodiment the probe may carry a binding moiety, or the label may be a binding moiety, that will allow manipulation of the probe and any amplification product hybridised thereto. Suitable binding moieties are discussed above.

Preferably any unbound label, e.g. in the form of a labelled oligonucleotide probe, will be separated from the amplification product before the detection step. This can be by any convenient means, for instance with one or more washing steps (e.g. with water or a buffered solution which may contain formamide and/or a detergent), electrophoresis, centrifugation, capture onto solid supports, chromatography or any combination thereof. Suitable solid supports are described above.

If the amplification method used is itself quantitative, e.g. amplification methods in which internal standards and controls are incorporated (for instance qPCR) the method of this aspect of the invention can also provide quantitative data. In these embodiments the method can even affix a numerical value to the prokaryote content of a sample. One such internal standard would be to amplify one or more (e.g. at least 2, 3, 5, or 10) samples of known prokaryote content under the same conditions as the test sample to provide a standard curve plotting amount of amplification product against number of organisms. The amount of amplification product obtained in the test sample can then be translated into a numerical value for the amount of prokaryotic organisms in the sample.

In other embodiments, the progress of the amplification reaction can be followed in real-time and the amplification profile can be compared with amplification profiles from samples of known prokaryote content or of known quantities of target sequence. In other embodiments the cycle threshold ($C_T$) can be used to calculate the amount of target sequence and therefore prokaryote content. In all qPCRs there is a threshold at which the fluorescence of the amplification product is detected above background. The cycle at which this threshold is crossed is the $C_T$. In the exponential phase of the reaction the quantity of DNA theoretically doubles every cycle and so relative amounts of DNA can be calculated between samples by comparing $C_T$ values falling in the exponential phase. If the comparison is made with samples with a known quantity of template, the quantity of template in the test sample can be calculated and the prokaryote content can be measured By analysing the amplification product in other ways, the method of the invention can be applied to the identification (e.g. taxonomic classification) and/or quantification of specific prokaryotes that might be in a sample.

Although 16S rRNA has regions that are conserved amongst prokaryotes, there are also hypervariable regions (regions V1 to V9) that contain sequences of nucleotides that are specific to individual taxonomic groupings of prokaryotes, e.g. divisions, classes, families, genera and species. By detecting the presence of such characteristic nucleotide sequences in the amplified product, or measuring the amount of such characteristic nucleotide sequences the presence of a particular taxonomic group of a prokaryote, e.g. division, class, family, genus or species can be verified and, in some embodiments, quantified.

Thus, provided herein is a method for determining the taxonomic classification of a prokaryotic organism in a sample, said method comprising (i) contacting the sample with an oligonucleotide primer comprising the nucleotide sequence of SEQ ID NO 1 or a nucleotide sequence capable of hybridising under high stringency conditions to the sequence complementary to SEQ ID NO 1 and an oligonucleotide primer comprising the nucleotide sequence of SEQ ID NO 2 or a nucleotide sequence capable of hybridising under high stringency conditions to the sequence complementary to SEQ ID NO 2 and performing a primer-dependent nucleic acid amplification reaction to amplify a target nucleotide sequence in the 16S rRNA or the 16S rDNA in a sample; and (ii) analysing the amplification product of step (i) to detect the presence or absence of a nucleotide sequence characteristic of a prokaryotic organism belonging to a specific taxonomic grouping.

The detection of the presence or absence of a nucleotide sequence characteristic of a prokaryotic organism belonging to a specific taxonomic grouping in the amplification product contributes to determining the taxonomic classification of a prokaryotic organism in the sample.

This method can also be considered a method for verifying the identity of a prokaryotic organism in a sample and so the detection of the presence or absence of a nucleotide sequence characteristic of a prokaryotic organism belonging to a specific taxonomic grouping in the amplification product contributes to verifying the identity of a prokaryotic organism in the sample.

The analysis of the amplification product can be done in a convenient way. For example, by using oligonucleotide probes that hybridise selectively to a nucleotide sequence in the amplification product which is characteristic of prokaryotes belonging to a specific taxonomic grouping; by using oligonucleotide probes that hybridise to the amplification product and which can be labelled selectively in the presence of a nucleotide sequence characteristic of a prokaryote belonging to a specific taxonomic grouping; by using nucleic acid sequencing techniques to obtain sequence information from the amplification product and comparing that to known sequences characteristic of prokaryotes belonging to a specific taxonomic grouping; or by performing nested PCR on the amplification product with one or more primers capable of hybridising selectively to a sequence characteristic of prokaryotes belonging to a specific taxonomic grouping. Of course, the skilled man would know of or be able to devise other approaches to analyse the amplification product.

Thus, in another aspect, provided herein is a method for verifying the identity of a prokaryotic organism in a sample, said method comprising (i) contacting the sample with an oligonucleotide primer comprising the nucleotide sequence of SEQ ID NO 1 or a nucleotide sequence capable of hybridising under high stringency conditions to the sequence complementary to SEQ ID NO 1; and an oligonucleotide primer comprising the nucleotide sequence of SEQ ID NO 2 or a nucleotide sequence capable of hybridising under high stringency conditions to the sequence complementary to SEQ ID NO 2 and performing a primer-dependent nucleic acid amplification reaction to amplify a target nucleotide sequence in the 16S rRNA or the 16S rDNA in a sample;

(ii) contacting the amplification product with one or more oligonucleotide probes that each hybridise selectively to a nucleotide sequence characteristic of prokaryotes belonging to a specific taxonomic grouping; and (iii) detecting hybridisation to the amplification product of the one or more oligonucleotide probes.

This method can also be considered a method for determining the taxonomic classification of a prokaryotic organism in a sample.

In this aspect, the nucleotide sequence characteristic of prokaryotes belonging to a specific taxonomic grouping, to which the oligonucleotide probe selectively hybridises, will be present in the amplification product obtained when 16S rRNA or 16S rDNA from prokaryotes belonging to that specific taxonomic grouping are amplified by the oligonucleotide primers of the invention.

In this aspect the oligonucleotide probes are designed, or selected, to hybridise (preferably under high stringency conditions) to a subregion of 16S rRNA or 16S rDNA from prokaryotes belonging to a specific taxonomic grouping which is in the target nucleotide sequence that is amplified by the oligonucleotide primers of the invention; and is therefore in the amplification product obtained when 16S rRNA or 16S rDNA from prokaryotes belonging to that specific taxonomic grouping is amplified by the oligonucleotide primers of the invention.

The presence or absence of hybridisation of the particular oligonucleotide probe(s) used to the amplification product thereby provides information to enable the skilled man to verify the identity (e.g. determine the taxonomic classification) of the prokaryotic organism. Preferably the oligonucleotide probes carry a label that will allow detection by direct means or indirect means. Suitable labels are described above. In preferred embodiments the label is selected such that it is detectable only when the probe is hybridised to its target. Conveniently, the oligonucleotide probes can be provided on a solid support, e.g. those described previously.

Preferably a plurality of uniquely labelled probes are used and preferably each probe hybridises selectively to a different nucleotide sequence that is characteristic of prokaryotes belonging to a specific taxonomic grouping (e.g. division, class, family, genus or species).

In another preferred embodiment a plurality of labelled probes arranged on a solid support with a defined spatial relationship are used. In this embodiment each probe may carry a unique label and preferably each probe hybridises selectively to a different nucleotide sequence that is characteristic of prokaryotes belonging to a specific taxonomic grouping. In preferred embodiments the label is selected such that it is detectable only when the probe is hybridised to its target.

In another preferred embodiment each of a plurality of probes (which may be labelled or unlabelled) will be immobilised on a particle, e.g. a bead, or a microsphere, having a particular label such that a population, or plurality of populations, of particles having the same label and the same probe immobilised thereon is formed. Detection of a hybridisation event occurring on a particle with a particular label will provide information on the sequence of the probe involved in that event.

In another aspect, in place of the steps (ii) and (iii) discussed previously, the amplification product may be contacted with one or more oligonucleotide probes that hybridise to the amplification product and which can be labelled selectively in the presence of a nucleotide sequence characteristic of a prokaryote belonging to a specific taxonomic grouping. In some embodiments the probe may already carry a label that is different to the label used to selectively label the probe. Subsequent detection of selectively labelled probe(s), or absence of selectively labelled probes, thereby provides information to enable the skilled man to verify the identity of (e.g. classify taxonomically) the prokaryotic organism. Conveniently selective labelling may be achieved using labelled nucleotides, i.e. by incorporation into the oligonucleotide probe a nucleotide carrying a label. In other words, selective labelling may occur by chain extension of the oligonucleotide probe using a polymerase enzyme which incorporates a labelled nucleotide, preferably a labelled dideoxynucleotide (e.g. ddATP, ddCTP, ddGTP, ddTTP, ddUTP) more preferably labelled ddCTP, most preferably a TAMRA labelled ddCTP. This approach to the detection of specific nucleotide sequences is sometimes referred to as primer extension analysis. Suitable primer extension analysis techniques are well known to the skilled man, e.g. those techniques disclosed in WO99/50448, the contents of which are incorporated herein by reference. Suitable labels are described above.

In preferred embodiments the selectively labelled oligonucleotide probe is detected after a step in which the oligonucleotide probes from the selective labelling step (i.e. labelled and unlabelled), or the selectively labelled oligonucleotide probes only, are hybridised to a sequence that is partially, or preferably fully, complementary to the oligonucleotide probe. Conveniently, the complementary sequence can be provided on a solid support, e.g. those described previously.

Preferably a plurality of probes are used and preferably each probe is labelled selectively in the presence of a different nucleotide sequence that is characteristic of prokaryotes belonging to a specific taxonomic grouping (e.g. division, class, family, genus or species). Each probe may be labelled with the same or different labels.

In another preferred embodiment a plurality of different complementary sequences arranged on a solid support with a defined spatial relationship are used.

In this embodiment each complementary sequence corresponds to a different oligonucleotide probe that may be labelled selectively in the presence of a nucleotide sequence characteristic of a prokaryote belonging to a specific taxonomic grouping.

As mentioned above in the methods of this aspect, the complementary sequences used therein can be provided on a solid support. In one convenient embodiment that solid support can be a membrane strip on to which the complementary sequences may be spotted (e.g. in a defined spatial relationship) and UV cross-linked, or DNA chips (microchips, glass chips) now common in molecular biology procedures. In another convenient embodiment that solid support can be particulate, e.g. beads and microspheres. Preferably each complementary sequence will be immobilised on a particle, e.g. a bead or a microsphere, having a particular label such that a population, or plurality of populations, of particles having the same label and the same complementary sequence immobilised thereon is formed. Detection of a hybridisation event occurring on a particle with a particular label will provide information on the sequence of the probe involved in that event.

The particles may be labelled in any convenient way, e.g. using one or more of the labels described above. In one embodiment the particle label will not be or comprise an oligonucleotide, or a nucleic acid, or a labelled oligonucleotide or labelled nucleic acid. Conveniently the particulate solid support of these embodiments will be labelled with a dye, e.g. a luminescent (e.g. bioluminescent, chemiluminescent, photoluminescent, radioluminescent, sonoluminescent, etc.) dye, or a plurality of dyes (or proportions thereof) which combine to give a unique electromagnetic spectral signature upon excitation. Signatures based on the absorption of certain wavelengths of electromagnetic radiation are also envisaged.

Conveniently the dye will be fluorescent, e.g. comprise red or infrared fluorophores, e.g. phycoerythrin.

The label may be immobilised on and/or in the particle, e.g. by direct covalent binding to the substrate of the particle or it may be bound to another molecule which is in turn immobilised on and/or in the particle. The label may also be incorporated into and/or onto the particle by non-covalent means, e.g. by entrapment, absorption or adsorption of the molecules making up the label in or on the substrate of the particle, or by entrapment in void(s) within the substrate and/or on its surface.

In other embodiments the particle comprises nanoparticles on which and/or in which the label has been immobilised or incorporated.

The label can be applied to the particle after it is produced, or the label may be incorporated or immobilised into and/or onto the particle during its production, e.g. during the cross-linking of a polymeric substrate.

Preferably the label of the probe(s) will be distinguishable from the label of the particle(s). In preferred embodiments the label of the particles will be detectable at the same time as the label of the probe(s). Preferably the labelled particles will also be magnetic, e.g. paramagnetic or superparamagnetic.

Suitable particulate solid supports are manufactured by Luminex Corp. See for instance WO01/13120, WO01/13119, WO97/14028 and WO99/19515, the contents of which are incorporated herein by reference. Further particles which may be used in the working on the invention are provided in U.S. Pat. Nos. 4,267,234, 4,267,235, 4,552,812, 4,677,138, 5,194,300, 4,774,189, 5,073,498, 4,717,655, 5,723,218, 5,326,692, 5,716,855, 5,573,909 and U.S. Pat. No. 5,786,219, the contents of which are incorporated herein by reference. Other suitable solid supports are manufactured by Illumina, Inc. See for instance WO00/39587, WO 01/18524, WO01/59432 and WO02/00336 the contents of which are incorporated herein by reference.

As described above, these aspects may be performed in ways that permit quantification of the amount of the prokaryotic organism, the identity of which is being verified or taxonomic classification being determined.

In another aspect, in place of the steps (ii) and (iii) discussed previously, the amplification product is sequenced by any convenient means and the sequence information is compared with entries in a nucleic acid sequence database to identify the source of the template and therefore verify the identity (determine the taxonomic classification) of a prokaryotic organism in the sample. Suitable sequencing methods are standard techniques and so are completely familiar to the skilled man. Suitable databases are freely available from online sources.

The sequencing of the amplification product can be performed directly on the amplification product, allowing for any necessary washing and/or sample manipulation steps. In other embodiments the amplification product can be cloned into a suitable cell type in order to prepare colonies containing copies of a single amplification product that may then be sequenced. This process will typically involve inserting the amplification product into a suitable nucleic acid vector, e.g. the TOPO TA Cloning® kit marketed by Invitrogen™, although the skilled man would be aware of many others, and transforming receptive cells, e.g. bacterial cells, fungal cells, insect cells or mammalian cells, e.g. *E. coli*, with the vector. After preparing colonies, e.g. homogeneous colonies, of transformed cells the colonies may be picked and the vector contained therein, which in turn contains a copy of the amplification product, sequenced.

In another aspect, in place of the steps (ii) and (iii) discussed previously, the amplification product is subjected to a further amplification reaction in which one or more nested oligonucleotide primers capable of hybridising selectively to a nucleotide sequence that is characteristic of prokaryotes belonging to a specific taxonomic grouping are used. By "nested" it is meant that the oligonucleotide primer hybridises to the amplification product in the target nucleotide sequence contained therein, which is between the two oligonucleotide primers of the preceding amplification reaction. It will be apparent to the skilled man that one of the nested oligonucleotide primers of this aspect of the invention could have the same nucleotide sequence as the oligonucleotide probe characteristic of prokaryotes belonging to a specific taxonomic grouping described above, or be based on that sequence.

The successful production of an amplification product by the nested primer(s) is indicative of the presence of prokaryotic organisms containing nucleotide sequences to which the nested primer(s) selectively hybridise. As such nucleotide sequences are characteristic of prokaryotes belonging to a specific taxonomic grouping, the successful production of an amplification product by the nested primer(s) is indicative of the presence of prokaryotic organisms belonging to that particular taxonomic grouping.

As described above, this embodiment may be performed in ways that permit quantification of the amount of the prokaryotic organism, the identity of which is being verified or taxonomic classification being determined.

In these aspects, the "identity" or the "taxonomic classification" of the prokaryotic organism should be construed broadly to cover any taxonomic label that may be applied to the organism and which can be adequately distinguished by the methods of the invention and the molecular tools that may be used therein. Typically, identification will involve identifying the organism in terms of the name of the division, class, family, genus or species to which the organism belongs.

A taxonomic division is defined as a taxonomic category that is of higher rank (i.e. more inclusive) than class, but of lower rank (i.e. less inclusive) than kingdom; e.g. Gracilicutes, Firmicutes, Tenericutes and Mendosicutes.

A taxonomic class is defined as a taxonomic category that is of higher rank (i.e. more inclusive) than family, but lower rank (i.e. less inclusive) than division; e.g. Scotobacteria, Anoxyphotobacteria, Oxyphotobacteria, Mollicutes and Bacteroidetes.

A taxonomic family is defined as a taxonomic category of higher rank (i.e. more inclusive) than genus but of lower rank (i.e. less inclusive) than class. Non-limiting examples include Enterobacteriaceae, Pasteurellaceae, Mycoplasmataceae, Pseudomonadaceae, Chromatiaceae, Micrococcaceae, Methanobacteriaceae and Bacteroidaceae.

A taxonomic genus is defined as a taxonomic category of higher rank (i.e. more inclusive) than species but of lower rank (i.e. less inclusive) than family. Non-limiting examples include *Escherichia, Salmonella, Staphylococcus, Listeria, Bacillus, Hyphomicrobium, Entamoeba, Toxoplasma, Giardia, Rhizopus, Blastomyces, Saccharomyces* and *Bacteroides*.

A taxonomic species is defined as a taxonomic category of higher rank (i.e. more inclusive) than subspecies but of lower rank (i.e. less inclusive) than genus. Non-limiting examples include *Escherichia coli, Salmonella typhi, Staphylococcus aureus, Listeria monocytogenes, Bacillus subtillis, Entamoeba histolytica, Rhizopus stolonifer, Blastomyces dermatitidis, Saccharomyces cerevisiae* and *Bacteroides fragilis*. Further examples are provided in Tables 1, 9 and 11.

As discussed above, the methods of the invention have applicability in all technical fields in which information on the level of prokaryotic organisms present in a sample and information on the identity of the prokaryotic organisms in a sample is required. Therefore the samples to which the methods of the invention may be applied are not limited. Thus, the invention covers both medical and non-medical applications.

For instance, the sample may be an environmental sample or a clinical sample from a subject. Environmental samples may include samples being monitored for biological safety or in which the microbial content is indicative of the quality or integrity of the sample or the surrounding environment, e.g. hydrocarbon stores, timber and wood. Thus, environmental samples include, but are not limited to, water samples (e.g. from lakes, rivers, seas, sewage plants and other water-treatment centres) soil samples, hydrocarbon samples, timber, wood (in particular timber or wood to be used, or which is being used, as structural material) biomass samples, effluent samples, industrial waste, commercial waste, domestic waste and samples from any stage of the human or animal food chain. The methods are of particular utility in the analysis of food and pharmaceutical samples and generally in health and hygiene applications where it is desired to monitor levels of microorganisms that give rise to infections and disease, food poisoning or food spoilage, e.g. in areas where food is being prepared or stored or where patients are being treated (e.g. healthcare institutions, hospitals, surgeries, clinics, etc). Similarly, microorganisms can contribute to the failure of structural timber and wood and the present invention can be used to identify the presence of, or monitor the levels of, such microorganisms in structural wood and timber, or products containing wood and timber.

The sample may also be a clinical sample taken from, or provided by, a subject. Clinical samples may include, but are not limited to, body fluids (e.g. blood, plasma, serum, cerebrospinal fluid, GI tract contents, semen, urine, stool/faecal); tissues (e.g. adrenal, hepatic, renal, pancreatic, pituitary, thyroid, immune, ovarian, testicular, prostate, endometrial, ocular, mammary, adipose, epithelial, endothelial, neural, muscle, pulmonary, epidermis, osseous) as well as samples obtained by e.g. a swab, rinse or scrape of a body cavity or biopsy. The invention is particularly suited to the analysis of samples from the GI tract of a subject, it is especially suited to the identification of normal and pathogenic microflora in the GI tract.

The subject may be any human or non-human animal subject, but more particularly may be a vertebrate, e.g. an animal selected from mammals, birds, amphibians, fish and reptiles. The animal may be a livestock or a domestic animal or an animal of commercial value, including laboratory animals or an animal in a zoo or game park. Representative animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, cod, haddock, sea bass and carp. Veterinary applications of the invention are thus covered. The subject may be viewed as a patient. Preferably the subject is a human.

The sample may be used in the methods of the invention in the form in which it was initially retrieved. The sample may also have undergone some degree of manipulation, refinement or purification before being used in the methods of the invention. Thus the term "sample" also includes preparations thereof, e.g. relatively pure or partially purified starting materials, such as semi-pure preparations of the above mentioned samples. The term "sample" also includes preparations of the above mentioned samples in which, the RNA of which, e.g. 16 S rRNA, has undergone reverse transcription.

The purification may be slight, for instance amounting to no more than the concentration of the solids, or cells, of the sample into a smaller volume or the separation of cells from some or all of the remainder of the sample. Representative cell isolation techniques are described in WO98/51693 and WO01/53525.

In other embodiments the invention uses a preparation of the nucleic acid from the above mentioned samples. Such preparations include reverse transcription products of such samples or nucleic acid preparations thereof. Techniques for the isolation of nucleic acid from samples, including complex samples, are numerous and well known in the art and described at length in the literature. The techniques described in WO98/51693 and WO01/53525 can also be employed to prepare nucleic acids from the above mentioned samples.

These preparations include relatively pure or partially purified nucleic acid preparations.

In a further aspect the invention provides the use of (i) an oligonucleotide primer comprising the nucleotide sequence of SEQ ID NO 1 or a nucleotide sequence capable of hybridising under high stringency conditions to the sequence complementary to SEQ ID NO 1; and (ii) an oligonucleotide primer comprising the nucleotide sequence of SEQ ID NO 2 or a nucleotide sequence capable of hybridising under high stringency conditions to the sequence complementary to SEQ ID NO 2 in the methods of the invention.

In a further aspect the invention provides a primer pair consisting of (i) an isolated oligonucleotide comprising the nucleotide sequence of SEQ ID NO 1 or a nucleotide sequence capable of hybridising under high stringency conditions to the sequence complementary to SEQ ID NO 1; and (ii) an isolated oligonucleotide comprising the nucleotide sequence of SEQ ID NO 2 or a nucleotide sequence capable of hybridising under high stringency conditions to the sequence complementary to SEQ ID NO 2.

The primer pair may be combined with any of the oligonucleotide probes described herein to create a primer probe set. For instance the primer probe set may comprise the primer pair and at least one oligonucleotide probe that hybridises selectively to a nucleotide sequence characteristic of prokaryotes belonging to a specific taxonomic grouping or an oligonucleotide probe that preferentially binds the amplification product obtained when 16S rRNA or 16S rDNA is amplified with the primers of the invention, or an oligonucleotide probe that preferentially binds to substantially all target nucleotide sequences that may be amplified by the primer pair of the invention. These oligonucleotides may be labelled as described above, e.g. with a moiety to assist with detection or manipulation. For instance the label may itself be a colorimetric, chemiluminescent, chromogenic, radioactive or fluorescent molecule, or be a colorimetric, luminescent, or chromogenic enzyme, or an antibody fragment, His-tag, biotin or streptavidin.

In other embodiments the primer probe set comprises at least one oligonucleotide probe that hybridises to the product of a nucleic acid amplification reaction in which the primer of the primer probe set are used and which permits selective labelling in the presence of a nucleotide sequence characteristic of a prokaryote belonging to a specific taxonomic grouping.

Some or all of the components of the primer pair and/or the primer probe set may be immobilised on any of the solid supports described above, e.g. particles, sheets, gels, filters, membranes, fibres, capillaries, chips or microtitre strips, slides, tubes, plates or wells. Preferably the support is magnetic, e.g. magnetic particles, for instance magnetic beads.

In a further aspect, provided is a complex comprising (i) an oligonucleotide primer comprising the nucleotide sequence of SEQ ID NO 1 or a nucleotide sequence capable of hybridising under high stringency conditions to the sequence complementary to SEQ ID NO 1; and (ii) an oligonucleotide primer comprising the nucleotide sequence of SEQ ID NO 2 or a nucleotide sequence capable of hybridising under high stringency conditions to the sequence complementary to SEQ ID NO 2;

both hybridised to a 16S rRNA or fragment thereof or 16S rDNA or a fragment thereof.

The complex may further comprise any of the herein described oligonucleotide probes, nested primers and the modified versions thereof.

A fragment of 16S rRNA or 16S rDNA is any part of a 16S rRNA molecule or a 16S rDNA molecule that is capable of hybridising, preferably at high stringency, to the oligonucleotide primers of the invention. It can also be considered to be a truncated 16S rRNA molecule or a truncated 16S rDNA molecule that comprises regions of sequence complementary to the oligonucleotide primers of the invention. The truncation may be from either or both ends of the molecule.

In a further aspect, provided are kits comprising (i) an oligonucleotide primer comprising the nucleotide sequence of SEQ ID NO 1 or a nucleotide sequence capable of hybridising under high stringency conditions to the sequence complementary to SEQ ID NO 1; and (ii) an oligonucleotide primer comprising the nucleotide sequence of SEQ ID NO 2 or a nucleotide sequence capable of hybridising under high stringency conditions to the sequence complementary to SEQ ID NO 2.

The kits may be designed for use in the methods of the invention and may comprise further components. Each component may be provided in a separate compartments or vessels. In other embodiments the primer pair of the invention may be provided in a single compartment or vessel. Where convenient and practical, mixtures of components could be provided. The components may be provided in dry, e.g. crystallised, freeze dried or lyophilised, form or in solution, typically such liquid compositions will be aqueous and buffered with a standard buffer such as Tris, HEPES, etc.

The kit may also be provided with instructions for using the kit, or with directions for how instructions may be obtained.

The additional components can be any of the various components that may be used to put the methods of the invention into effect, e.g. any component discussed above. In a preferred embodiment the kit further comprises the probes and nested primers described above, preferably e.g. an oligonucleotide probe that hybridises to the product of a nucleic acid amplification reaction in which components (i) and (ii) are used and which permits selective labelling in the presence of a nucleotide sequence characteristic of a prokaryote belonging to a specific taxonomic grouping, and optionally means for selective labelling of the oligonucleotide probe, and optionally nucleotide sequences complementary to the oligonucleotide probes, preferably immobilised on a solid support. In another embodiment the kit further comprises a nucleic acid vector, into which the product of a nucleic acid amplification reaction in which components (i) and (ii) are used, may be inserted; and optionally cells which may be transformed by the vector. In this embodiment the kit may further comprise some or all of the means for sequencing the nucleic acid vector and the product of a nucleic acid amplification reaction in which components (i) and (ii) are used.

Further components might optionally be any or all of the means, e.g. buffers, enzymes etc. for performing an amplification reaction with the primers of the invention. For instance, the kits may optionally contain a PCR reaction buffer, nucleotide triphosphates, further oligonucleotide primers, or DNA polymerases, preferably a thermostable polymerase such as Taq polymerase.

Further components might optionally be any or all of the means, e.g. buffers, enzymes etc. for performing a reverse transcription reaction. For instance a reverse transcriptase, RNA specific primers, an RT reaction buffer, and nucleotide triphosphates.

Further components might optionally be any or all of the means to take the sample. For instance such means might include dipsticks, biopsy apparatus, swabbing devices, pouches or vessels. Preferably these means will be provided in sterile form.

Further components might optionally be any or all of the means to purify or refine the sample. For instance means to isolate or concentrate cells in a sample, e.g. cell binding solid supports or filtration devices. In other embodiments the means to purify or refine the sample might be any or all of the means for extracting nucleic acid from a sample. For instance cell lysis reagents (e.g. chaotropic salts, alcohols, detergents, membrane altering compounds), nucleic acid binding solid supports (e.g. as described above) or nucleic acid precipitating agents (e.g. salts, alcohols)

Further components might optionally be any or all of the means to detect amplified nucleic acid. For instance the labels described herein (e.g. double stranded DNA binding dyes, labelled oligonucleotide probes), apparatus to detect these labels, electrophoresis materials and apparatus, or chromatography materials and apparatus.

The invention will be further described with reference to the following non-limiting Examples.

EXAMPLE 1

Materials/Methods

Bacteria:
Samples of single bacterial strains were obtained from the German Collection of Microorganisms and Cell Cultures (DSMZ). Strains analysed are listed in Table 1.

Genomic DNA Isolation:
Genomic DNA was isolated directly from freeze dried pellets of each strain with the Qiagen Blood and Tissue kit in accordance with the manufacturer's instructions.

TABLE 1

Bacterial samples and DNA concentration in ng/µl

| Sample Number | DSMZ Identifier | Scientific name | Conc. of DNA isolated (ng/µl) |
|---|---|---|---|
| 1 | 756 | Clostridium perfringens | 24.2 |
| 2 | 2079 | Bacterioides thetaiotamicron | 219.2 |
| 3 | 20021 | Lacrobacillus rhamnosus | 46.0 |
| 4 | 20079 | Lactobacillus acidophilus | 55.8 |
| 5 | 20088 | Bifidobacteruim longum subsp. infantis | 20.5 |
| 6 | 20219 | Bifidobacterium longum subsp longum | 12.1 |
| 7 | 20231 | Staphylococcus aureus subsp aureus | 55.4 |
| 8 | 20477 | Enterococcus faecium | 46.1 |
| 9 | 20478 | Enterococcus faecalis | 45.3 |
| 10 | 20735 | Veillonella dispar | 11.0 |
| 11 | 20739 | Veillonella atypicon | 12.5 |
| 12 | 30083 | Escherichia coli | 21.8 |
| 13 | 1402 | Clostridium ramosum | 36.4 |
| 14 | 1447 | Bacteroides vulgatus | 87.5 |
| 15 | 2151 | Bacterioides fragilis | 86.3 |
| 16 | 4688 | Campylobacter jejuni | 25.2 |
| 17 | 8978 | Haemophilus parainfl | 16.6 |
| 18 | 13772 | Salmonella bongori | 34.2 |
| 19 | 17058 | Salmonella ent | 51.5 |
| 20 | 17855 | Bacterioides breve | 18.3 |
| 21 | 20213 | Bifidobacterium dorei | 9.9 |
| 22 | 20565 | Streptococcus pyog | 18.7 |
| 23 | 20566 | Streptococcus pneu | 17.7 |
| 24 | 20567 | Streptococcus sang | 14.7 |
| 25 | 20600 | Listeria monocytogenes | 11.2 |
| 26 | 20701 | Parabacterioides distas | 12.9 |
| 27 | 30104 | Kleibsiella pneu | 43.4 |

PCR Primers:
The sequences of the 16S rRNA gene amplification primers used herein are recited in Table 2. Versions of the 16SKR8F and 16SU1510R primers containing chemically modified bases called LNA (Locked Nucleic Acid, represented as capital letters in the sequences displayed in Table 2) were used (KR8F/U1510R). These primers have a higher annealing temperature (lower melting temperature) than unmodified versions.

TABLE 2

Primer sequences

| Name | Sequence 5'-3' | Tm | GC % | SEQ ID NO |
|---|---|---|---|---|
| 16SKR8F | aag agt ttg atc atg gct ca | 48 | 40 | 3 |
| 16SU1510R | cgg tta cct tgt tac gac tt | 50 | 45 | 2 |
| KR8F | aag aGT tTg aTc aTg gct ca | 66 | 40 | 4 |
| U1510R | cgg Tta ccT tgT Tac gac tt | 67 | 45 | 6 |
| MangalaF-1 | tcc tac ggg agg cag cag | 55 | 67 | 1 |
| 16S8 FA | gagagtttgatcgctca | 45 | 47 | 6 |
| 16S8 FB | aagagtttgatcctggctca | 50 | 45 | 7 |
| 16S8 FC | gagggttcgattgtcgctca | 54 | 55 | 8 |

PCR Setup:
HOT FIREPol DNA Polymerase (Solis BioDyne) and KlenTaq (DNA Polymerase Technology) were used in accordance with manufacture's recommendations:

TABLE 3

| | µl | Final concentration |
|---|---|---|
| Hot FirePol (5 U/µl) | 5 | 5 U |
| 10x B2 buffer | 2.5 | 1x |
| MgCl$_2$ (25 mM) | 2.5 | 2.5 mM |
| dNTP (10 mM) | 0.5 | 200 µM |
| F primer (10 µM) | 0.5 | 0.2 µM |
| R primer (10 µM) | 0.5 | 0.2 µM |
| template | 1 | 10-200 ng |
| H$_2$O | 12.5 | |
| total volume | 25 | |

TABLE 4

| Initial denaturation | 95° C. | 15 s |
|---|---|---|
| Denaturation | 95° C. | 30 s |
| Annealing | 55° C. | 30 s |
| Elongation | 72° C. | 90 s |
| Final elongation | 72° C. | 7 min |

(Denaturation, annealing and elongation steps repeated 30x before final elongation)

TABLE 5

| | µl | Final concentration |
|---|---|---|
| KlenTaq (25 U/µl) | 0.2 | 5 U |
| 10X buffer (35 mM MgCl$_2$) | 3 | 3.5 mM |
| dNTP (10 mM) | 1 | 200 µM |
| F primer (10 µM) | 1 | 0.2 µM |
| R primer (10 µM) | 1 | 0.2 µM |
| template | 1 | 10-200 ng |
| H$_2$O | 17.8 | |
| total volume | 25 | |

TABLE 6

| | | |
|---|---|---|
| Initial denaturation | 94° C. | 2 min |
| Denaturation | 95° C. | 30 s |
| Annealing | 55° C. | 30 s |
| Elongation | 68° C. | 3 min |
| Final elongation | 72° C. | 7 min |

(Denaturation, annealing and elongation steps repeated 30x before final elongation)

The PCR products (5 μl) were resolved by electrophoresis on 1.5% agarose gels in 1×TAE buffer. The gels were then stained with ethidium bromide and visualized under UV light using a Kodak Molecular Imaging System.

EXAMPLE 2

Primer Combination 16SKR8F and 16SU1510R

Figure 1:
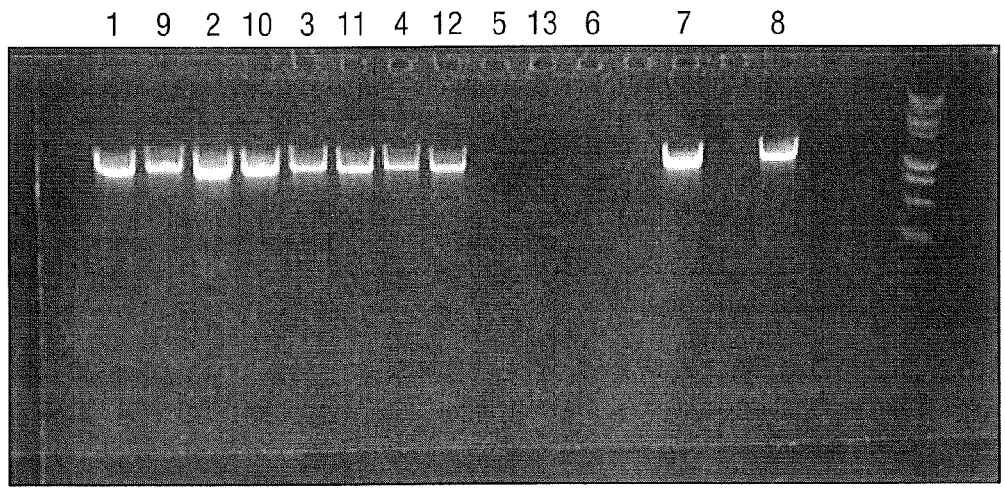
FIG. 1 is a photograph of a gel on which the products of the PCR amplification of DNA from sample numbers 1 to 12

DNA from sample numbers 1 to 12 (lanes 1 to 12) and negative control (lane 13) was amplified with the KlenTaq DNA Polymerase as described above using the 16SKR8F and 16SU1510R primers and resolved on agarose gel as described above. The results are shown in FIG. 1. FIG. 1 shows that 10 samples gave one single and strong PCR band, however the two *Bifidobacterium* samples (lanes 5 and 6) show no PCR product. This shows that the primer combination 16SKR8F and 16SU1510R is not capable of amplifying 16S rDNA from all bacteria.

EXAMPLE 3

Primer Combination KR8F and U1510R (LNA Modified 16SKR8F and 16SU1510R)

The KR8F and U1510R primers were used with the Klentaq enzyme to amplify DNA templates from *Bacterioides fragilis*, *Bifidobacterium longum* spp *longum* and *Escherichia coli* (with template-free negative control) in a gradient PCR where the annealing temperature was set at a temperature of between 55 and 70° C. The annealing time was set to 1 minute in this experiment. Results are shown in FIG. 2 (key to Figure recited in Tables 7 and 8). FIG. 2 shows that the LNA modified versions of 16SKR8F and 16SU1510R also could not amplify *Bifidobacterium* rDNA. The use of LNA did not allow a higher annealing temperature to be used successfully as the strongest bands detected on gel was at 55.5° C., which was the same as for the same primers without LNA modification.

TABLE 7

| Row | Sample |
|---|---|
| A | *Bacterioides fragilis* |
| B | *Bifidobacterium longum* spp *longum* |
| C | *Escherichia coli* |
| D | negative control (H$_2$O as template) |

TABLE 8

| Lane | Annealing temp (° C.) |
|---|---|
| 1 | 55.1 |
| 2 | 55.5 |
| 3 | 56.3 |
| 4 | 57.7 |
| 5 | 59.4 |
| 6 | 61.4 |
| 7 | 63.3 |

TABLE 8-continued

| Lane | Annealing temp (° C.) |
|---|---|
| 8 | 65.3 |
| 9 | 67.6 |
| 10 | 69.0 |
| 11 | 69.7 |
| 12 | 70.2 |

EXAMPLE 4

Primer Combinations of Primers 16S8 FA, 16S8 FB or 16S8 FC and 16SU1510R

The annealing sequence of the 16S8KRF primer in 16S rDNA does contain some point mutations in certain bacterial strains. *Bifidobacterium* is one such example. Three different nested primers were constructed with the objective of finding a better forward primer that could work together with the 16SU1510R primer. The three nested primers were called 16S8FA, 16S8FB and 16S8FC.

The experiment described in Example 2 was repeated with either 16S8FA, 16S8FB or 16S8FC in place of 16SKR8F. Results are shown in FIG. 3. Like the primer combination 16SKR8F and 16SU1510R the pairing of 16S8FA or 16S8FB and 16SU1510R was unable to amplify the two *Bifidobacterium* samples (lanes 5 and 6). The primer pair 16S8FC and 16SU1510R amplified all but sample 6 although the lack of amplification of sample 6 could be due to the lack of template in the reaction.

To further characterise the 16S8FC and 16SU1510R primer pair, DNA from sample numbers 13 to 27 (lanes 13 to 27) and negative control (lane C) was amplified with the KlenTaq DNA Polymerase as described above using the 16S8FC and 16SU1510R primers and resolved on agarose gel as described above. The results are shown in FIG. 4. FIG. 4 shows that samples 17, 18 and 19 (*Haemophilus parainfl*, *Salmonella bongori*, *Salmonella* ent) gave no PCR product. This shows that the primer combination 16S8FC and 16SU1510R is not capable of amplifying 16S rDNA from all bacteria.

EXAMPLE 5

Primer Combination of Primers 16S8 FA, 16S8 FB, 16S8 FC and 16SU1510R

The first stage of Example 4 was repeated using all of the nested primers (16S8FA, 16S8FB and 16S8FC) together with 16S U1510R. Results are shown in FIG. 5. FIG. 5 shows that all samples but sample 12 can be amplified using this primer combination. However the reactions using samples 1 to 12 display more than a single PCR product. This is an indication that non-specific hybridisation is occurring and giving rise to non-target amplification products and so this primer combination clearly is not ideal. More fundamentally, the use four primers in amplification reactions is significantly less preferable to using two.

EXAMPLE 6

Primer Combination MangalaF-1 and 16SU1510R

MangalaF-1 is the Mangala F sequence with the 3' nucleotide removed. This was predicted to lower the melting temperature of the primer.

All 27 templates were subjected to PCR as described above. Results are shown in FIG. 6. FIG. 6 shows that all samples but sample 6 can be amplified using this primer combination. Sample 12 also showed a lower amount of product than other samples. However, after isolating more DNA from sample 6 (*Bifidobacterium longum longum*) and sample 12 (*E. coli*) and repeating the experiment these two samples also gave strong and specific PCR bands (FIG. 7).

EXAMPLE 7

The experiment described in Example 6 was repeated with further prokaryotes to further validate the primer combination of MangalaF-1 and 16U1510R. Specific amplification products from the following prokaryotes have been obtained, data not shown.

TABLE 9

| Species | DSMV Identifier |
|---|---|
| *Clostridium leptum* | 753 |
| *Clostridium saccharolyticum* | 2544 |
| *Sphingobacterium spiritivorum* | 2582 |
| *Mobiluncus mulieris* | 2710 |
| *Mobiluncus curtisii* | 2711 |
| *Syntrophococcus sucromutans* | 3224 |
| *Eubacterium cylindroides* | 3983 |
| *Chryseobacterium gleum* | 5567 |
| *Clostridium scindens* | 5676 |
| *Clostridium xylanolyticum* | 6555 |
| *Bacteroides uniformis* | 6597 |
| *Prevotella melaninogenica* | 7089 |
| *Capnocytophaga ochracea* | 7271 |
| *Clostridium fimetarium* | 9179 |
| Lachno *Pseudobutyrivibrio ruminis* | 9787 |
| Lachno *Blautia hydrogenotrophica* | 10507 |
| *Granulicatella elegans* | 11693 |
| *Clostridium xylanovorans* | 12503 |
| *Bulleidia extructa* | 13220 |
| *Clostridium hiranonis* | 13275 |
| *Colllinsella intestinalis* | 13280 |
| *Lachnobacterium bovis* strain | 14045 |
| *Bryantella formatexigens* | 14469 |
| *Shuttleworthia satelles* | 14600 |
| *Anaerostipes caccae* | 14662 |
| *Hespellia porcina* | 15481 |
| *Atopobium vaginae* | 15829 |
| *Roseburia inulinivorans* | 16841 |
| *Prevotella marshii* | 16973 |
| *Bacteroides plebeius* | 17135 |
| *Bacteroides coprocola* | 17136 |
| *Pseudomonas gessardii* | 17152 |
| *Anaerotruncus colihominis* | 17241 |
| *Oribacterium sinus* | 17245 |
| *Bacteroides finegoldii* | 17565 |
| *Clostridium glycyrrhizinilyticum* | 17593 |
| *Eubacterium rectale* | 17629 |
| *Faecalibacterium prausnitzii* | 17677 |
| *Peptostreptococcus stomatis* | 17678 |
| *Bacteroides massiliensis* | 17679 |
| *Parabacteroides johnsonii* | 18315 |
| *Prevotella oris* | 18711 |

TABLE 9-continued

| Species | DSMV Identifier |
|---|---|
| *Gordonibacter pamelaeae* | 19378 |
| *Parabacteroides merdae* | 19495 |
| *Prevotella oralis* | 20702 |

EXAMPLE 8

Freeze dried bacteria were purchased from either DSMZ (Deutsche Sammlung von Mikroorganismen and Zellkulturen GmbH—German Collection of Microorganisms) or CCUG (Culture Collection University of Goteborg) as indicated in Table 11. The bacteria were lysed by mechanical lysis using glass beads (<106 µm, Sigma) and DNA captured and purified on SiMAG/MP-DNA Magnetic Beads (Chemicell) according to manufacturer's recommendations.

PCR was carried out with the primer pairs listed in Table 10 below, using 1 µl of DNA template, 1.25 U of HOT FIREpol® DNA polymerase (Solis BioDyne), HOT FIREpol® buffer B2 (Solis BioDyne), 2.5 mM $MgCl_2$, 0.2 mM dNTP mix and 0.2 µM of each of the primers used.

TABLE 10

The primers used in Example 8

| Primer pair | Primer Name | Sequence 5'-3' | SEQ ID NO |
|---|---|---|---|
| A | 16SU1510R | cgg tta cct tgt tac gac tt | 2 |
| A | Mangala-1 | tcc tac ggg agg cag cag | 1 |
| B | 27F | agagtttgatcctggctcag | 9 |
| B | 1492R | ggttaccttgttacgactt | 10 |
| C | 8F | agagtttgatcctgg | 11 |
| C | 1542R | aaaggaggtgatcca | 12 |
| D | R1378 | cggtgtgtacaaggcccgggaacg | 13 |
| D | F27 | agagtttgatcmtggctcag* | 14 |

*m = a or c (a mixture of primers either with a or c at the m position were used in experiments)

PCR reactions were carried with an initial incubation step at 95° C. for 15 min, followed by 30 cycles of 95° C. for 30 sec, 55° C. for 30 sec and 60° C. for 1 min 20 sec. A final elongation step was performed at 72° C. for 7 min. For Primer pair B, a second PCR was run with an annealing temperature of 50° C. Amplification at either temperature is indicated as a PCR product in Table 11.

The PCR product was visualized by gel electrophoresis. A band with similar intensity as the control is indicated as Good (G), while a considerably weaker band is indicated as Low (L) amount of DNA.

TABLE 11

Summary of PCR results using primer pairs of Table 10

| PCR No. | Culture Origin | Culture ID | Strain name | Pair A | Pair B | Pair B | Pair C | Pair D |
|---|---|---|---|---|---|---|---|---|
| 1 | DSM | 21505 | *Acidsminococcus intestini* | G | G | N | N | N |
| 2 | DSM | 30007 | *Acinetobacter baumannii* | G | G | G | N | L |
| 3 | DSM | 6964 | *Acinetobacter junii* | G | G | G | N | G |
| 4 | DSM | 6963 | *Acinetobacter* sp. | G | G | G | N | G |

TABLE 11-continued

Summary of PCR results using primer pairs of Table 10

| PCR No. | Culture Origin | Culture ID | Strain name | Pair A | Pair B | Pair B | Pair C | Pair D |
|---|---|---|---|---|---|---|---|---|
| 5 | DSM | 15803 | *Actinomyces cardiffensis* | G | N | G | N | G |
| 6 | DSM | 15434 | *Actinomyces urogenitalis* | L | L | G | N | L |
| 7 | DSM | 15272 | *Aeromicrobium marinum* | G | — | N | — | — |
| 8 | CCUG | 14551 | *Aeromonas hydrophila* ss hydro | G | — | L | — | — |
| 9 | DSM | 19176 | *Aeromonas sobria* | G | G | G | N | N |
| 10 | DSM | 22959 | *Akkersmania municiphila* | G | G | G | N | G |
| 11 | DSM | 30033 | *Alcaligenes faecalis* | N | L | L | N | N |
| 12 | DSM | 17216 | *Alistipes putredinis* | G | L | N | N | L |
| 13 | DSM | 19121 | *Alistipes shahii* | G | L | L | — | — |
| 14 | DSM | 13181 | *Anaerobaculum mobile* | L | L | G | N | L |
| 15 | DSM | 7454 | *Anaerococcus hydrogenalis* | G | G | G | G | L |
| 16 | DSM | 20548 | *Anaerococcus prevotii* | G | G | G | L | L |
| 17 | DSM | 17244 | *Anaerofustis stercorihominis* | G | G | G | G | L |
| 18 | CCUG | 44773 | *Anaeroglobus geminatus* | G | G | G | N | G |
| 19 | DSM | 14662 | *Anaerostipes caccae* | G | G | G | L | G |
| 20 | DSM | 14662 | *Anaerostipes caccae* | G | G | G | — | — |
| 21 | DSM | 17241 | *Anaerotruncus colihominis* | G | G | G | G | L |
| 22 | DSM | 5562 | *Aneurinibacillus aneurinilyticus* | G | N | L | — | — |
| 23 | DSM | 7090 | *Atopobium rimae* | G | N | G | N | G |
| 24 | DSM | 15829 | *Atopobium vaginae* | G | G | G | N | G |
| 25 | DSM | 485 | *Bacillus alcalophilus* (13012010) | N | N | N | N | N |
| 26 | CCUG | 38735 | *Bacterioides caccae* | N | G | G | — | — |
| 27 | DSM | 17855 | *Bacterioides dorei* | G | G | G | N | G |
| 28 | DSM | 2151 | *Bacterioides fragilis* | L | N | N | N | N |
| 29 | DSM | 19555 | *Bacterioides stercoris* | G | G | G | N | N |
| 30 | DSM | 2079 | *Bacterioides thetaiotamicron* | G | G | G | N | G |
| 31 | DSM | 1447 | *Bacterioides vulgatus* | G | G | G | N | G |
| 32 | CCUG | 15402 | *Bacteroides capillosus* | G | G | G | N | G |
| 33 | DSM | 14838 | *Bacteroides cellulosilyticus* | G | G | G | N | G |
| 34 | DSM | 17136 | *Bacteroides coprocola* | G | G | N | N | N |
| 35 | DSM | 18228 | *Bacteroides coprophilus* | G | G | G | N | G |
| 36 | DSM | 20697 | *Bacteroides eggerthii* | G | G | G | — | — |
| 37 | DSM | 17565 | *Bacteroides finegoldii* | G | N | G | N | G |
| 38 | DSM | 3978 | *Bacteroides galacturonicus* | G | G | G | — | — |
| 39 | DSM | 17393 | *Bacteroides intestinalis* | G | G | G | N | G |
| 40 | DSM | 17679 | *Bacteroides massiliensis* | G | G | G | N | G |
| 41 | DSM | 1896 | *Bacteroides ovatus* | G | G | G | — | — |
| 42 | DSM | 17135 | *Bacteroides plebeius* | G | G | L | N | G |
| 43 | DSM | 6597 | *Bacteroides uniformis* | G | G | G | N | G |
| 44 | DSM | 18836 | *Bacteroides xylanisolvens* | G | G | G | N | N |
| 45 | DSM | 20219 | *Bifid. longum* subsp *longum* | G | N | L | N | N |
| 46 | DSM | 20088 | *Bifid. longum* subsp. *infantis* | G | L | G | N | N |
| 47 | DSM | 20083 | *Bifidobacterium adolescentis* | G | N | G | N | N |
| 48 | DSM | 20098 | *Bifidobacterium angulatum* | G | L | G | N | L |
| 49 | DSM | 20456 | *Bifidobacterium bifidum* | G | N | G | N | N |
| 50 | DSM | 20213 | *Bifidobacterium breve* | G | N | N | N | L |
| 51 | DSM | 16992 | *Bifidobacterium catenulatum* | G | N | L | N | N |
| 52 | DSM | 20436 | *Bifidobacterium dentium* | G | N | L | N | N |
| 53 | CCUG | 34979 | *Bifidobacterium gallicum* | G | N | G | N | G |
| 54 | DSM | 20438 | *Bifidobacterium pseudocatenulatum* | G | — | L | — | — |
| 55 | DSM | 935 | *Blautia coccoides* | G | G | G | N | G |
| 56 | DSM | 20583 | *Blautia hansenii* | G | G | G | — | — |
| 57 | DSM | 9583 | *Brevibacterium mcbrellneri* | G | G | G | N | G |
| 58 | DSM | 14469 | *Bryantella formatexigens* | G | G | G | L | G |
| 59 | DSM | 13220 | *Bulleidia extructa* | G | G | G | L | L |
| 60 | DSM | 21774 | *Burkholderia oklahomensis* | G | G | L | L | G |
| 61 | DSM | 2876 | *Butyrivibrio crossotus* | G | G | G | — | — |
| 62 | DSM | 3071 | *Butyrivibrio fibrisolvens* | L | L | N | N | N |
| 63 | DSM | 9716 | *Campylobacter concisus* | G | G | G | L | L |
| 64 | DSM | 6644 | *Campylobacter curvus* | G | G | G | L | G |
| 65 | DSM | 4688 | *Campylobacter jejuni* | G | G | G | G | G |
| 66 | DSM | 3290 | *Capnocytophaga gingivalis* | G | G | G | N | G |
| 67 | DSM | 7271 | *Capnocytophaga ochracea* | G | G | G | N | G |
| 68 | DSM | 7273 | *Capnocytophaga sputigena* | G | G | G | N | N |
| 69 | DSM | 15897 | *Catenibacterium mitsuokai* | G | G | G | G | G |
| 70 | DSM | 4568 | *Cedecea davisae* | G | G | G | N | G |
| 71 | CCUG | 46254 | *Cetobacterium somerae* | G | G | G | N | L |
| 72 | DSM | 5567 | *Chryseobacterium gleum* | G | G | G | N | G |
| 73 | DSM | 17578 | *Citrobacter youngae* | G | L | G | N | G |
| 74 | DSM | 12273 | *Clostridium algidixylanolyticum* | G | L | G | N | L |
| 75 | DSM | 12857 | *Clostridium amygdalinum* | G | G | G | L | G |
| 76 | DSM | 15981 | *Clostridium asparagiforme* | G | G | G | L | G |
| 77 | DSM | 16795 | *Clostridium bartlettii* | G | G | G | G | G |
| 78 | DSM | 15670 | *Clostridium bolteae* | G | G | L | N | L |
| 79 | DSM | 1785 | *Clostridium celatum* | G | L | G | — | — |

TABLE 11-continued

Summary of PCR results using primer pairs of Table 10

| PCR No. | Culture Origin | Culture ID | Strain name | Pair A | Pair B | Pair B | Pair C | Pair D |
|---|---|---|---|---|---|---|---|---|
| 80 | DSM | 7528 | *Clostridium chauvoei* | G | N | N | N | N |
| 81 | DSM | 1296 | *Clostridium difficile* | G | L | G | N | G |
| 82 | DSM | 9179 | *Clostridium fimetarium* | G | G | G | L | G |
| 83 | DSM | 17593 | *Clostridium glycyrrhizinilyticum* | G | G | L | G | G |
| 84 | DSM | 13479 | *Clostridium hathewayi* | G | G | G | N | G |
| 85 | DSM | 13275 | *Clostridium hiranonis* | G | G | G | G | G |
| 86 | DSM | 2158 | *Clostridium histolyticum* | G | G | G | N | G |
| 87 | DSM | 15053 | *Clostridium hylemonae* | G | L | G | N | L |
| 88 | DSM | 755 | *Clostridium indolis* | G | G | L | N | G |
| 89 | DSM | 15929 | *Clostridium jejuense* | G | G | G | G | G |
| 90 | DSM | 753 | *Clostridium leptum* | G | G | L | N | G |
| 91 | DSM | 12182 | *Clostridium methoxybenzovorans* | G | G | G | N | L |
| 92 | DSM | 5476 | *Clostridium methylpentosum* | G | G | G | L | G |
| 93 | DSM | 6740 | *Clostridium orbiscindens* | L | L | L | N | L |
| 94 | DSM | 2630 | *Clostridium paraputrificum* | G | N | G | — | — |
| 95 | DSM | 756 | *Clostridium perfringens* | G | G | L | N | G |
| 96 | DSM | 1402 | *Clostridium ramosum* | G | G | G | N | G |
| 97 | DSM | 2544 | *Clostridium saccharolyticum* | G | G | G | G | G |
| 98 | CCUG | 45363 | *Clostridium scindens* | L | — | G | — | — |
| 99 | DSM | 5676 | *Clostridium scindens* | G | G | G | G | G |
| 100 | DSM | 7534 | *Clostridium septicum* | G | — | L | — | — |
| 101 | DSM | 15981 | *Clostridium* sp. | G | G | G | — | — |
| 102 | DSM | 632 | *Clostridium sphenoides* | L | N | N | N | N |
| 103 | DSM | 1552 | *Clostridium spiroforme* | G | G | G | — | — |
| 104 | DSM | 795 | *Clostridium sporogenes* | G | G | G | N | G |
| 105 | DSM | 46282 | *Clostridium sporogenes* | G | L | G | N | G |
| 106 | DSM | 934 | *Clostridium symbiosum* | G | G | G | — | — |
| 107 | DSM | 6555 | *Clostridium xylanolyticum* | G | G | G | N | G |
| 108 | DSM | 12503 | *Clostridium xylanovorans* | G | G | G | L | G |
| 109 | DSM | 3979 | *Collinsella aerofaciens* | L | N | G | N | N |
| 110 | DSM | 13279 | *Collinsella* sp. | N | G | G | N | G |
| 111 | DSM | 13280 | *Colllinsella intestinalis* | L | G | G | N | L |
| 112 | ATCC | 27758 | *Coprococcus comes* | G | — | G | — | — |
| 113 | ATCC | 27759 | *Coprococcus eutactus* | G | — | G | — | — |
| 114 | DSM | 44532 | *Corynebact. aurimucosum* | N | N | N | N | N |
| 115 | DSM | 44120 | *Corynebact. glucuronolyticum* | N | N | N | N | N |
| 116 | DSM | 44291 | *Corynebact. lipophiloflavum* | N | N | N | N | N |
| 117 | DSM | 7171 | *Corynebacterium jeikeium* (15012010) | N | N | N | N | N |
| 118 | DSM | 20668 | *Corynebacterium striatum* | N | N | N | N | N |
| 119 | DSM | 17581 | *Delftia tsuruhatensis* | G | G | G | G | G |
| 120 | DSM | 10664 | *Desulfitobacterium hafniense* | G | G | G | L | N |
| 121 | DSM | 749 | *Desulfomonas pigra* | G | L | L | N | G |
| 122 | DSM | 4024 | *Desulfotomaculum guttoideum* | G | G | L | N | G |
| 123 | DSM | 15470 | *Dialister invisus* | G | G | G | L | G |
| 124 | DSM | 13814 | *Dorea longicatena* | G | L | L | N | L |
| 125 | DSM | 13814 | *Dorea longicatena* | G | G | G | L | L |
| 126 | DSM | 30052 | *Edwardsiella tarda* | G | G | G | N | N |
| 127 | DSM | 2243 | *Eggerthella lenta* | L | L | N | N | G |
| 128 | DSM | 8340 | *Eikenella corrodens* | G | G | G | N | N |
| 129 | DSM | 30053 | *Enterobacter aerogenes* | G | G | G | N | N |
| 130 | DSM | 17580 | *Enterobacter cancerogenus* | G | G | G | L | G |
| 131 | DSM | 12409 | *Enterobacter hormaechei* | G | G | G | N | G |
| 132 | CCUG | 53905 | *Enterobacter hormaechei oharae* | G | G | G | N | G |
| 133 | DSM | 20478 | *Enterococcus faecalis* | G | G | G | L | L |
| 134 | DSM | 20477 | *Enterococcus faecium* | G | G | G | L | L |
| 135 | DSM | 5055 | *Erypeothrix rhusiopathiae* | G | G | G | G | G |
| 136 | DSM | 17582 | *Escherichia albertii* | G | G | G | N | G |
| 137 | DSM | 30083 | *Escherichia coli* | G | G | G | N | N |
| 138 | DSM | 3979 | *Eubacterium aerofaciens* (=*Collinsella aerofaciens*) | N | N | N | N | L |
| 139 | DSM | 3989 | *Eubacterium biforme* | G | N | G | L | G |
| 140 | DSM | 3983 | *Eubacterium cylindroides* | G | G | G | L | G |
| 141 | DSM | 3991 | *Eubacterium dolichum* | G | L | G | L | G |
| 142 | DSM | 3353 | *Eubacterium hallii* | G | G | G | N | G |
| 143 | DSM | 4000 | *Eubacterium plautii* | G | G | G | L | G |
| 144 | DSM | 15684 | *Eubacterium ramulus* | G | G | G | N | G |
| 145 | DSM | 17629 | *Eubacterium rectale* | G | G | L | N | L |
| 146 | DSM | 15702 | *Eubacterium siraeum* | G | G | G | — | — |
| 147 | DSM | 17677 | *Faecalibacterium prausnitzii* | L | G | L | L | N |
| 148 | DSM | 20470 | *Finegoldia magna* | G | G | G | N | N |
| 149 | DSM | 19810 | *Fusobacterium gonidiaformans* | G | G | G | — | — |
| 150 | DSM | 19679 | *Fusobacterium nucleatum* | G | G | G | N | G |
| 151 | DSM | 19545 | *Fusobacterium periodonticum* | G | G | G | N | N |
| 152 | DSM | 4944 | *Gardnerella vaginalis* | L | N | N | N | N |

TABLE 11-continued

Summary of PCR results using primer pairs of Table 10

| PCR No. | Culture Origin | Culture ID | Strain name | Pair A | Pair B | Pair B | Pair C | Pair D |
|---|---|---|---|---|---|---|---|---|
| 153 | CCUG | 37817 | Gemella bergeri | G | G | G | G | G |
| 154 | CCUG | 53991 | Gemella haemolysans | G | G | G | N | G |
| 155 | CCUG | 37820 | Gemella sanguinis | G | G | G | N | G |
| 156 | DSM | 19378 | Gordonibacter pamelaeae | G | L | L | N | N |
| 157 | DSM | 11693 | Granulicatella elegans | G | G | G | G | G |
| 158 | DSM | 30163 | Hafnia alvei | G | G | G | N | L |
| 159 | CCUG | 47163 | Helicobacter canadensis | G | G | G | N | G |
| 160 | DSM | 5359 | Helicobacter cinaedi | G | G | N | G | G |
| 161 | DSM | 21031 | Helicobacter pylori | G | G | L | N | N |
| 162 | DSM | 15481 | Hespellia porcina | G | G | G | G | G |
| 163 | DSM | 12042 | Holdemania filiformis | G | G | G | G | G |
| 164 | DSM | 5175 | Klebsiella oxytoca | G | G | G | L | G |
| 165 | DSM | 4798 | Klebsiella oxytoca | G | G | G | N | L |
| 166 | DSM | 30104 | Kleibsiella pneu | G | G | G | L | G |
| 167 | DSM | 15831 | Labctobacillus sakei ssp. Carnosus | G | G | G | L | G |
| 168 | DSM | 10507 | Lachno Blautia hydrogenotrophica | G | G | G | N | G |
| 169 | DSM | 14534 | Lachno Blautia luti | G | G | G | — | — |
| 170 | DSM | 10518 | Lachno Blautia schinkii | G | G | G | N | G |
| 171 | DSM | 5434 | Lachno Clostridium aerotolerans | G | — | L | — | — |
| 172 | DSM | 5628 | Lachno Clostridium celerecrescens | G | G | G | L | G |
| 173 | DSM | 933 | Lachno Clostridium clostridioforme | G | G | G | — | — |
| 174 | DSM | 6011 | Lachno Clostridium colinum | G | — | G | G | G |
| 175 | DSM | 1787 | Lachno Clostridium nexile | G | G | G | G | G |
| 176 | DSM | 5832 | Lachno Clostridium populeti | G | — | G | L | G |
| 177 | DSM | 3992 | Lachno Dorea formicigenerans | G | G | G | L | G |
| 178 | DSM | 3982 | Lachno Eubacterium contortum | G | — | G | L | G |
| 179 | DSM | 3988 | Lachno Eubacterium ventriosum | G | L | G | G | G |
| 180 | DSM | 9787 | Lachno Pseudobutyrivibrio ruminis | G | G | G | G | G |
| 181 | DSM | 14610 | Lachno Roseburia intestinalis | G | G | G | — | — |
| 182 | DSM | 12504 | Lachno Sporobacterium olearium | G | G | G | L | G |
| 183 | DSM | 14045 | Lachnobacterium bovis strain | G | G | G | G | G |
| 184 | DSM | 20021 | Lacrobacillus rhamnosus | G | G | L | L | G |
| 185 | DSM | 20054 | Lactobacillus brevis | G | L | G | N | G |
| 186 | DSM | 20584 | Lactobacillus crispatus | G | G | L | L | G |
| 187 | DSM | 20079 | Lactobacillus acidophilus | G | G | G | N | G |
| 188 | DSM | 11664 | Lactobacillus amylolyticus | G | G | G | L | G |
| 189 | DSM | 16041 | Lactobacillus antri | G | G | G | — | — |
| 190 | DSM | 20057 | Lactobacillus buchneri | G | G | G | L | G |
| 191 | DSM | 20011 | Lactobacillus casei | G | G | G | L | G |
| 192 | DSM | 14060 | Lactobacillus coleoohomnis | G | G | G | G | G |
| 193 | DSM | 20080 | Lactobacillus delbrueckii ssp bulgaricus | G | G | G | — | — |
| 194 | DSM | 20052 | Lactobacillus fermentum | G | L | N | N | N |
| 195 | DSM | 20243 | Lactobacillus gasseri | G | N | G | N | N |
| 196 | DSM | 20075 | Lactobacillus helveticus | G | G | G | L | G |
| 197 | DSM | 20176 | Lactobacillus hilgardii | G | G | G | N | G |
| 198 | DSM | 13335 | Lactobacillus iners | G | N | G | G | G |
| 199 | DSM | 20557 | Lactobacillus jensenii | G | G | G | L | L |
| 200 | DSM | 10533 | Lactobacillus johnsonii | G | G | G | N | G |
| 201 | DSM | 5622 | Lactobacillus paracasei | G | G | G | G | G |
| 202 | DSM | 5622 | Lactobacillus paracasei (13012010) | G | G | G | G | G |
| 203 | DSM | 20205 | Lactobacillus plantarum | G | G | G | N | G |
| 204 | DSM | 20053 | Lactobacillus reuteri | G | L | G | N | L |
| 205 | DSM | 20403 | Lactobacillus ruminis | G | L | G | N | L |
| 206 | DSM | 20554 | Lactobacillus salivarius | L | N | G | N | N |
| 207 | DSM | 16047 | Lactobacillus ultunensis | G | N | G | L | L |
| 208 | DSM | 5837 | Lactobacillus vaginalis | L | G | G | L | G |
| 209 | DSM | 14985 | Laribacter hongkongensis | G | N | N | N | N |
| 210 | DSM | 19756 | Leptotrichia goodfellowii | G | G | G | N | G |
| 211 | DSM | 21651 | Leptotrichia hofstadii | G | G | G | N | L |
| 212 | DSM | 19758 | Leptotrichia wadei | G | G | G | L | G |
| 213 | DSM | 20346 | Leuconostoc mesenteroides ssp. Cremoris | G | G | G | L | G |
| 214 | DSM | 20601 | Listeria grayi strain | G | N | G | L | G |
| 215 | DSM | 20649 | Listeria innocua | G | G | G | N | G |
| 216 | DSM | 20600 | Listeria monocytogenes | G | G | G | G | G |
| 217 | DSM | 1672 | Megamonas hypermegale | G | G | G | N | G |
| 218 | DSM | 17226 | Megasphaera micronuciformis | G | L | G | N | N |
| 219 | DSM | 2374 | Methanobrevibacter smithii | N | G | N | N | N |
| 220 | DSM | 861 | Methanobrevibacter smithii | L | N | N | N | N |
| 221 | DSM | 3091 | Methanosphaera stadtmanae | G | N | L | N | N |
| 222 | DSM | 20544 | Mitsukoella multiacida | G | L | G | L | L |
| 223 | DSM | 2711 | Mobiluncus curtisii | G | G | G | N | G |
| 224 | DSM | 2710 | Mobiluncus mulieris | L | L | L | N | G |
| 225 | DSM | 30164 | Morganella morganii | G | G | G | N | L |

TABLE 11-continued

Summary of PCR results using primer pairs of Table 10

| PCR No. | Culture Origin | Culture ID | Strain name | Pair A | Pair B | Pair B | Pair C | Pair D |
|---|---|---|---|---|---|---|---|---|
| 226 | DSM | 44648 | *Mycobact. parascrofulaceum* | N | N | N | G | N |
| 227 | DSM | 19104 | *Mycoplasma hominis* | G | G | G | — | — |
| 228 | DSM | 17610 | *Neisseria subflava* | G | G | G | G | G |
| 229 | DSM | 17245 | *Oribacterium sinus* | G | G | G | G | G |
| 230 | DSM | 20701 | *Parabacterioides distas* | G | G | G | N | N |
| 231 | DSM | 19495 | *Parabacterioides merdae* | G | G | G | N | G |
| 232 | DSM | 18315 | *Parabacteroides johnsonii* | G | G | G | N | L |
| 233 | DSM | 19495 | *Parabacteroides merdae* | G | G | G | N | G |
| 234 | CCUG | 38734 | *Parabacteroides merdae* | G | G | G | — | — |
| 235 | DSM | 10105 | *Parascardovia denticolens* | N | N | N | N | N |
| 236 | DSM | 15970 | *Parasporobacterium paucivorans* | G | G | G | L | G |
| 237 | DSM | 20468 | *Parvimonas micra* | G | G | L | N | N |
| 238 | DSM | 20238 | *Pediococcus acidilactici* | G | G | N | N | N |
| 239 | CCUG | 52631 | *Pelomonas aquatica* | G | L | G | N | G |
| 240 | DSM | 17678 | *Peptostreptococcus stomatis* | G | G | L | G | G |
| 241 | DSM | 14760 | *Phascolarctobacterium faecium* | G | G | G | G | G |
| 242 | DSM | 20709 | *Porphyromonas gingivalis* | G | G | G | N | G |
| 243 | CCUG | 16442 | *Porpyromonas endodontalis* | L | — | G | — | — |
| 244 | CCUG | 53648 | *Prevotella amnii* | G | — | G | — | — |
| 245 | DSM | 18205 | *Prevotella copri* | G | G | G | — | — |
| 246 | DSM | 16973 | *Prevotella marshii* | G | G | G | N | G |
| 247 | DSM | 7089 | *Prevotella melaninogenica* | G | G | G | N | G |
| 248 | DSM | 20702 | *Prevotella oralis* | G | G | G | N | G |
| 249 | DSM | 18711 | *Prevotella oris* | G | G | G | N | L |
| 250 | DSM | 18206 | *Prevotella stercorea* | G | L | G | N | G |
| 251 | CCUG | 50105 | *Prevotella timonensis* | G | N | G | N | G |
| 252 | CCUG | 15452 | *Prevotella veroralis* | G | — | G | — | — |
| 253 | DSM | 30116 | *Proteus mirabilis* | L | N | N | N | N |
| 254 | DSM | 4544 | *Proteus penneri* | G | G | G | N | G |
| 255 | DSM | 13387 | *Proteus vulgaris* | G | G | G | N | G |
| 256 | DSM | 30120 | *Providencia alcalifaciens* | G | G | G | N | L |
| 257 | DSM | 4542 | *Providencia rettgeri* | G | G | G | N | G |
| 258 | DSM | 4541 | *Providencia rustigianii* | G | G | G | N | G |
| 259 | DSM | 4539 | *Providencia stuartii* | G | G | G | N | G |
| 260 | DSM | 17152 | *Pseudomonas gessardii* | G | G | L | N | G |
| 261 | DSM | 3980 | *Pseudoramibacter alactolyticus* | G | G | G | L | G |
| 262 | CCUG | 55836 | *Pyramidobacter piscolens* | G | G | G | N | G |
| 263 | DSM | 13640 | *Ralstonia* sp. | G | G | G | G | G |
| 264 | DSM | 7464 | *Raoultella ornithinolytica* | G | G | G | N | L |
| 265 | DSM | 18184 | *Rhodotrula mucilaginosa* | G | N | N | N | N |
| 266 | DSM | 16840 | *Roseburia faecis* | G | L | G | — | — |
| 267 | DSM | 16841 | *Roseburia inulinivorans* | G | G | G | G | G |
| 268 | CCUG | 39066 | *Roseomonas cervicalis* | G | L | G | N | G |
| 269 | DSM | 43762 | *Rothia dentocariosa* | L | L | L | N | G |
| 270 | DSM | 20455 | *Ruminococcus albus* | G | G | G | L | G |
| 271 | DSM | 13772 | *Salmonella bongori* | G | G | G | N | G |
| 272 | DSM | 17058 | *Salmonella ent* | G | G | G | N | G |
| 273 | DSM | 17058 | *Salmonella enteritidis* | G | G | G | N | G |
| 274 | DSM | 10107 | *Scardovia inopinata* | G | G | G | N | L |
| 275 | DSM | 19578 | *Selenomonas noxia* | G | G | G | N | G |
| 276 | DSM | 20758 | *Selenomonas sputigena* | G | G | G | N | N |
| 277 | DSM | 30121 | *Serratia marcescens* | G | G | G | N | N |
| 278 | CCUG | 9565 | *Shigella dysenteriae* | G | G | G | N | G |
| 279 | DSM | 5570 | *Shigella sonnei* | G | G | G | N | G |
| 280 | DSM | 14600 | *Shuttleworthia satelles* | G | G | G | L | G |
| 281 | DSM | 2579 | *Simonsiella muelleri* | G | G | G | N | G |
| 282 | DSM | 15923 | *Slackia exigua* | G | N | N | N | N |
| 283 | DSM | 2582 | *Sphingobacterium spiritivorum* | G | G | G | N | G |
| 284 | DSM | 20231 | *Staph. aureus* subsp *aureus* | G | G | G | L | L |
| 285 | DSM | 20044 | *Staphylococcus epidermidis* | G | G | G | N | N |
| 286 | DSM | 50170 | *Stenotrophomonas maltophilia* | G | G | G | N | N |
| 287 | DSM | 22957 | *Streptococcus infantarius* | G | G | G | L | G |
| 288 | DSM | 2134 | *Streptococcus agalactiae* | G | G | G | N | G |
| 289 | DSM | 20558 | *Streptococcus equinus* | G | G | G | N | N |
| 290 | DSM | 12643 | *Streptococcus mitis* | G | G | G | N | G |
| 291 | DSM | 20066 | *Streptococcus oralis* | G | G | G | L | G |
| 292 | DSM | 20566 | *Streptococcus pneu* | G | G | L | G | G |
| 293 | DSM | 20565 | *Streptococcus pyog* | G | G | G | L | L |
| 294 | DSM | 20567 | *Streptococcus sang* | G | G | G | G | G |
| 295 | DSM | 40313 | *Streptomyces albus* | N | N | N | N | N |
| 296 | DSM | 40090 | *Streptomyces lanatus* | N | N | N | N | N |
| 297 | DSM | 15176 | *Subdoligranulum variabile* | G | L | G | — | — |
| 298 | DSM | 3224 | *Syntrophococcus sucromutans* | G | G | G | N | G |
| 299 | DSM | 20739 | *Veillonella atypicon* | G | G | G | G | G |
| 300 | DSM | 20735 | *Veillonella dispar* | G | G | G | G | G |

TABLE 11-continued

Summary of PCR results using primer pairs of Table 10

| PCR No. | Culture Origin | Culture ID | Strain name | Pair A | Pair B | Pair B | Pair C | Pair D |
|---|---|---|---|---|---|---|---|---|
| 301 | DSM | 2008 | Veillonella parvula | G | G | G | N | G |
| 302 | DSM | 14823 | Victivallis vadensis | G | G | G | N | G |
| 303 | DSM | 20288 | Weissella paramesenteroides | G | G | G | L | G |
| 304 | DSM | 18582 | Yersina bercovieri | G | G | G | N | N |
| 305 | DSM | 4780 | Yersinia enterocolitica | G | G | G | N | G |
| 306 | CCUG | 32133 | Yersinia pestis | G | N | G | N | G |
| 307 | DSM | 8978 | Yersinia pseudotuberculosis | G | G | G | L | G |
| 308 | DSM | 5079 | Yokenella regensburgei | G | L | G | N | G |

TABLE 12

Key to and Summary of Table 11

|  | Pair A | Pair B 55° C. | Pair B 50° C. | Pair C | Pair D |
|---|---|---|---|---|---|
| N = No PCR product obtained | 15 | 42 | 31 | 178 | 59 |
| L = Low amount of PCR product obtained | 19 | 35 | 34 | 54 | 41 |
| G = Good band = High amount of PCR product obtained | 274 | 217 | 242 | 39 | 168 |
| No. of samples positive for PCR product (i.e. L or G results seen) | 293 | 252 | 276 | 93 | 209 |
| Not tested (—) | 0 | 14 | 0 | 37 | 37 |
| No. samples tested | 308 | 294 | 307 | 271 | 268 |
| Percent samples amplified with primer pair | 95.1% | 85.7% | 89.9% | 34.3% | 78.0% |

As can be seen from the results presented in Tables 11 and 12, the primer pair of the invention can successfully amplify the highest proportion of the bacterial species tested. The primer pair closest in terms of universality to the primer pair of the invention is Pair B. As can be seen, at 55° C. Pair B is only capable of amplifying 16S rDNA from 85.7% of the samples tested. At this more stringent, and hence preferred temperature, the primer pair of the invention is capable of amplifying nearly 10% more samples. Even at a less stringent temperature of 50° C. (the annealing temperature typically used with Pair B in the literature and the temperature calculated to be near optimal for Pair B) Pair B is still only capable of amplifying 16S rDNA from 89.9% of the samples tested. It is important to note that in the context of the vast overall number of different prokaryote (e.g. bacterial) specifies in existence, the difference in universality between the primer pair of the invention and primer pair B is hugely significant. It is expected that the primer pair of the invention used in its optimal conditions will amplify a greater proportion of prokaryotic species than other 16S primer pairs used in their optimal conditions.

The primer pair of the invention is capable of amplifying 16S rDNA from virtually all bacteria species tested and of the 15 samples (out of 308) from which 16S rDNA was not amplified, only 5 samples (Alcaligenes faecalis, Bacterioides caccae, Collinsella sp., Eubacterium aerofaciens (=Collinsella aerofaciens), and Mycobact. parascrofulaceum were amplified by any of the other primer pairs. It is also important to note that 7 of these 15 non-amplified species are derived from a only two genera (Corynebacterium and Streptomyces). That none of the primer pairs were capable of amplifying 16S rDNA from Corynebacterium or Streptomyces suggests that a fundamental incompatibility exists between bacteria from these genera and techniques designed to amplify 16S rDNA.

Notably the primer pair of the invention was uniquely able to amplify DNA from 9 samples of bacteria (Aeromicrobium marinum, Bacterioides fragilis, Clostridium chauvoei, Clostridium sphenoides, Gardnerella vaginalis, Laribacter hongkongensis, Proteus mirabilis, Rhodotrula mucilaginosa and Slackia exigua).

Also significantly, unlike Pair B, the primer pair of the invention is capable of amplifying 16S rDNA from Bifid. longum subsp longum and Bifidobacterium breve, two important bacteria to detect/analyse in faecal samples. Pair B is therefore unsuitable for use in the analysis of the prokaryote content of faecal samples because selectivity such as this will distort any data obtained.

Recitation of ranges of values herein are merely intended to serve as a shorthand method of referring individually to each separate value falling within the range, unless otherwise indicated herein, and each separate value is incorporated into the specification as if it were individually recited herein. The endpoints of all ranges directed to the same component or property are inclusive and independently combinable.

All methods described herein can be performed in a suitable order unless otherwise indicated or clearly contradicted by context. The use of any and all examples, or exemplary language (e.g., "such as") herein is intended to better illuminate the disclosure and is non-limiting unless otherwise specified. No language in the specification should be construed as indicating that any non-claimed element as essential to the practice of the claimed embodiments. Unless defined otherwise, technical and scientific terms used herein have the same meaning as is commonly understood by one of skill in the art to which this disclosure belongs.

Embodiments are described herein, including the best modes known to the inventors. Variations of such embodiments will become apparent to those of ordinary skill in the art upon reading the foregoing description. The skilled artisan is expected to employ such variations as appropriate, and the disclosed methods are expected to be practiced otherwise than as specifically described herein. Accordingly, all modifications and equivalents of the subject matter recited in the claims appended hereto are included to the extent permitted by applicable law. Moreover, any combination of the above-described elements in all possible variations thereof is encompassed unless otherwise indicated herein or otherwise clearly contradicted by context.

The invention claimed is:

1. A method of amplifying a target nucleotide sequence in 16S rRNA or in 16S rDNA comprising
   (a) contacting a sample comprising a 16S rDNA and/or the reverse transcription product of a 16S rRNA with an oligonucleotide primer consisting essentially of the nucleotide sequence of SEQ ID NO 1 and an oligonucleotide primer consisting essentially of the nucleotide sequence of SEQ ID NO 2; and
   (b) performing a primer-dependent nucleic acid amplification reaction to amplify the target nucleotide sequence in the 16S rRNA or the 16S rDNA.

2. A method for measuring the prokaryote content of a sample, said method comprising performing the method of claim 1 on said sample, and
   (c) detecting the amplification product of step (b) thereby detecting the 16S rRNA or 16S rDNA in the sample as a measure of the prokaryotic content of the sample.

3. A method for determining the taxonomic classification of a prokaryotic organism in a sample, said method comprising performing the method of claim 1 on said sample, and
   (c) analysing the amplification product of step (b) to detect the presence or absence of a nucleotide sequence characteristic of a prokaryotic organism belonging to a specific taxonomic grouping.

4. The method of claim 3 wherein step (c) comprises
   (i) contacting the amplification product with one or more oligonucleotide probes that each hybridise selectively to a nucleotide sequence characteristic of prokaryotes belonging to a specific taxonomic grouping; and
   (ii) detecting hybridisation to the amplification product of said probes.

5. The method of claim 4 wherein a plurality of uniquely labelled oligonucleotide probes are used in step (ii) and wherein each of the plurality of oligonucleotide probes hybridise selectively to a different nucleotide sequence that is characteristic of prokaryotes belonging to a specific taxonomic grouping.

6. The method of claim 3 wherein step (c) comprises
   (i) contacting the amplification product with one or more oligonucleotide probes that hybridise to the amplification product and which permit selective labelling in the presence of a nucleotide sequence characteristic of a prokaryote belonging to a specific taxonomic grouping;
   (ii) selectively labelling the oligonucleotide probe(s) in the presence of said nucleotide sequence;
   (iii) detecting the presence or absence of the labelled oligonucleotide probe(s).

7. The method of claim 6 wherein a plurality of oligonucleotide probes are used and wherein each probe is selectively labelled in the presence of a different nucleotide sequence that is characteristic of prokaryotes belonging to a specific taxonomic grouping.

8. The method of claim 6 wherein step (iii) comprises hybridisation of the oligonucleotide probe(s) from the labelling step to a sequence(s) complementary to the probe(s).

9. The method of claim 8 wherein the sequence complementary to the probe is provided on a solid support.

10. The method of claim 6 wherein the oligonucleotide probe(s) is labelled by incorporation of a labelled nucleotide.

11. The method of claim 3 wherein step (c) comprises
   (i) sequencing the amplification product; and
   (ii) comparing the sequence information obtained from step (i) with entries in a nucleic acid sequence database to determine the taxonomic classification of a prokaryotic organism in the sample.

12. The method of claim 11, further comprising prior to step (i), steps in which the amplification product is inserted into a nucleic acid vector, cells are transformed with said vector and transformed cell colonies are picked for sequencing.

13. The method of claim 3 wherein step (c) comprises subjecting the amplification product to a further primer-dependent nucleic acid amplification reaction in which one or more nested oligonucleotide primers capable of hybridising selectively to a nucleotide sequence that is characteristic of prokaryotes belonging to a specific taxonomic grouping are used.

14. The method of claim 1 wherein the sample is an environmental sample or a sample from, or provided by, a subject.

15. The method of claim 14 wherein the subject is a human.

16. The method of claim 1 wherein the primer-dependent nucleic acid amplification reaction is selected from PCR, LAR/LCR, SDA, Loop-mediated isothermal amplification and NASBA/3SR.

17. The method of claim 6, wherein the one or more oligonucleotide probes is labeled by incorporation of a labeled dideoxynucleotide.

* * * * *